US012109194B2

(12) United States Patent
Milner et al.

(10) Patent No.: US 12,109,194 B2
(45) Date of Patent: Oct. 8, 2024

(54) SYNERGISTIC COMBINATION THERAPY FOR TREATING ALS

(71) Applicant: BioJiva LLC, San Jose, CA (US)

(72) Inventors: Peter Milner, Los Altos, CA (US); Nadia Litterman, Los Altos, CA (US); Mark Midei, Los Altos, CA (US)

(73) Assignee: BioJiva LLC, San Jose, CA (US)

( * ) Notice: Subject to any disclaimer, the term of this patent is extended or adjusted under 35 U.S.C. 154(b) by 0 days.

(21) Appl. No.: 17/684,279

(22) Filed: Mar. 1, 2022

(65) Prior Publication Data

US 2022/0249442 A1    Aug. 11, 2022

Related U.S. Application Data

(63) Continuation-in-part of application No. PCT/US2022/015366, filed on Feb. 4, 2022, and a continuation-in-part of application No. 17/169,271, filed on Feb. 5, 2021, now Pat. No. 11,351,143.

(60) Provisional application No. 63/310,544, filed on Feb. 15, 2022, provisional application No. 63/310,541, filed on Feb. 15, 2022.

(51) Int. Cl.
A61K 31/4152 (2006.01)
A61K 31/202 (2006.01)
A61P 25/28 (2006.01)

(52) U.S. Cl.
CPC ........ A61K 31/4152 (2013.01); A61K 31/202 (2013.01); A61P 25/28 (2018.01)

(58) Field of Classification Search
None
See application file for complete search history.

(56) References Cited

U.S. PATENT DOCUMENTS

| | | | |
|---|---|---|---|
| 1,166,930 A | 1/1916 | Shchepinov | |
| 2,798,053 A | 7/1957 | Brown | |
| 3,520,872 A | 7/1970 | Wechter | |
| 3,755,560 A | 8/1973 | Dickert et al. | |
| 4,421,769 A | 12/1983 | Dixon et al. | |
| 4,509,949 A | 4/1985 | Huang et al. | |
| 4,599,379 A | 7/1986 | Flesher et al. | |
| 4,628,078 A | 12/1986 | Glover et al. | |
| 4,835,206 A | 5/1989 | Farrar et al. | |
| 4,849,484 A | 7/1989 | Heard | |
| 5,011,681 A | 4/1991 | Ciotti et al. | |
| 5,087,445 A | 2/1992 | Haffey et al. | |
| 5,100,660 A | 3/1992 | Hawe et al. | |
| 5,194,448 A | 3/1993 | Coupland et al. | |
| 5,436,269 A | 7/1995 | Yazawa et al. | |
| 5,709,888 A | 1/1998 | Gil et al. | |
| 5,843,497 A | 12/1998 | Sundram et al. | |
| 5,914,347 A | 6/1999 | Grinda | |
| 6,111,066 A | 8/2000 | Anderson, III et al. | |
| 6,331,532 B1 | 12/2001 | Murphy et al. | |
| 6,417,233 B1 | 7/2002 | Sears et al. | |
| 6,503,478 B2 | 1/2003 | Chaiken et al. | |
| 7,179,928 B2 | 2/2007 | Smith et al. | |
| 7,232,809 B2 | 6/2007 | Murphy et al. | |
| 7,432,305 B2 | 10/2008 | Miller et al. | |
| 7,470,798 B2 | 12/2008 | Wang et al. | |
| 7,514,461 B2 | 4/2009 | Wang et al. | |
| 7,888,334 B2 | 2/2011 | Murphy et al. | |
| 7,888,335 B2 | 2/2011 | Taylor et al. | |
| 10,052,299 B2 | 8/2018 | Shchepinov | |
| 10,058,522 B2 | 8/2018 | Shchepinov | |
| 10,058,612 B2 | 8/2018 | Shchepinov | |
| 10,154,983 B2 * | 12/2018 | Shchepinov | ......... A61K 31/232 |
| 10,730,821 B2 | 8/2020 | Vidovic et al. | |
| 11,351,143 B1 | 6/2022 | Milner et al. | |
| 2001/0023259 A1 | 9/2001 | Slabas et al. | |
| 2002/0052342 A1 | 5/2002 | Murphy et al. | |
| 2002/0081689 A1 | 6/2002 | Yan et al. | |
| 2002/0198177 A1 | 12/2002 | Horrobin | |
| 2003/0032078 A1 | 2/2003 | Travis | |
| 2003/0069208 A1 | 4/2003 | Murphy et al. | |
| 2004/0043013 A1 | 3/2004 | McCleary | |
| 2004/0106579 A1 | 6/2004 | Murphy et al. | |
| 2005/0043553 A1 | 2/2005 | Smith et al. | |
| 2005/0164908 A1 | 7/2005 | Ginsberg et al. | |
| 2005/0245487 A1 | 11/2005 | Murphy et al. | |
| 2006/0035382 A1 | 2/2006 | Shinozaki et al. | |
| 2006/0205685 A1 | 9/2006 | Phiasivongsa et al. | |
| 2006/0229278 A1 | 10/2006 | Taylor et al. | |
| 2006/0241088 A1 | 10/2006 | Arterburn et al. | |

(Continued)

FOREIGN PATENT DOCUMENTS

| | | |
|---|---|---|
| CN | 1114878 A | 1/1996 |
| EP | 0713653 A1 | 5/1996 |

(Continued)

OTHER PUBLICATIONS

Cho et al. "Role of Edaravone as a Treatment Option for Patients with Amyotrophic Lateral Sclerosis," Pharmaceuticals 2021, 1-14, 29 published Dec. 31, 2020. (Year: 2020).*
McGeer et al. "Pharmacologic Approaches to the Treatment of Amyotrophic Lateral Sclerosis," Biodrugs 2005; 19 (1): 31-37 (Year: 2005).*
Mitsumoto et al. "Drug combination treatment in patients with ALS: Current status and future directions," Neurology 1996;47(Suppl 2):S1034107. (Year: 1996).*
May 17, 2023 (WO) International Search Report & Written Opinion PCT/US2023/013051.

(Continued)

Primary Examiner — Jeffrey S Lundgren
Assistant Examiner — Michael J Schmitt
(74) Attorney, Agent, or Firm — Banner & Witcoff, Ltd.

(57) ABSTRACT

Disclosed are methods for inhibiting the progression of amyotrophic lateral sclerosis (ALS) in humans. The methods use a synergistic combination of 3-methyl-1-phenyl-2-pyrazoline-5-one and deuterated arachidonic acid or a prodrug thereof, such as 11,11-D2-linoleic acid or an ester thereof.

18 Claims, 1 Drawing Sheet

(56) References Cited

U.S. PATENT DOCUMENTS

| | | |
|---|---|---|
| 2007/0004639 A1 | 1/2007 | Kane et al. |
| 2007/0032548 A1 | 2/2007 | Ellis |
| 2007/0238709 A1 | 10/2007 | Murphy et al. |
| 2007/0270381 A1 | 11/2007 | Murphy et al. |
| 2008/0161267 A1 | 7/2008 | Taylor et al. |
| 2008/0234197 A1 | 9/2008 | Allam et al. |
| 2008/0275005 A1 | 11/2008 | Murphy et al. |
| 2009/0054504 A1 | 2/2009 | Bozik et al. |
| 2009/0069354 A1 | 3/2009 | Czarnik |
| 2009/0181367 A1 | 7/2009 | Cote et al. |
| 2009/0182022 A1 | 7/2009 | Rongen et al. |
| 2009/0215896 A1 | 8/2009 | Morseman et al. |
| 2009/0232916 A1 | 9/2009 | Shulman et al. |
| 2009/0258841 A1 | 10/2009 | Murphy et al. |
| 2009/0280516 A1 | 11/2009 | Chen et al. |
| 2009/0306015 A1 | 12/2009 | Gately et al. |
| 2009/0326070 A1 | 12/2009 | Freeman et al. |
| 2010/0022645 A1 | 1/2010 | Nelson et al. |
| 2010/0029706 A1 | 2/2010 | Miller et al. |
| 2010/0056643 A1 | 3/2010 | Bachynsky et al. |
| 2010/0160248 A1 | 6/2010 | Shchepinov |
| 2010/0168051 A1 | 7/2010 | Malik |
| 2011/0028434 A1 | 2/2011 | Destaillats et al. |
| 2011/0028493 A1 | 2/2011 | Matsunaga et al. |
| 2011/0046219 A1 | 2/2011 | Hlinman et al. |
| 2011/0082206 A1 | 4/2011 | Miller |
| 2011/0092592 A1 | 4/2011 | Yano |
| 2011/0105609 A1 | 5/2011 | Shchepinov |
| 2011/0144051 A1 | 6/2011 | Von Borstel |
| 2011/0189212 A1 | 8/2011 | Harats et al. |
| 2011/0190195 A1 | 8/2011 | Atlas |
| 2012/0005765 A1 | 1/2012 | Kumar et al. |
| 2013/0309330 A1 | 11/2013 | Mastronardi |
| 2014/0044692 A1 | 2/2014 | Shchepinov |
| 2014/0044693 A1 | 2/2014 | Shchepnov |
| 2014/0050712 A1 | 2/2014 | Shchepinov |
| 2014/0099648 A1 | 4/2014 | Walker et al. |
| 2014/0147428 A1 | 5/2014 | Shchepinov |
| 2016/0303150 A1 | 10/2016 | Megiddo |
| 2018/0318261 A1 | 11/2018 | Yang et al. |
| 2019/0046491 A1 | 2/2019 | Shchepinov |
| 2019/0046644 A1 | 2/2019 | Shchepinov |
| 2019/0054052 A1 | 2/2019 | Shchepinov |
| 2019/0231733 A1 | 8/2019 | Shchepinov |
| 2019/0282529 A1 | 9/2019 | Shchepinov |
| 2021/0069144 A1 | 3/2021 | Shchepinov |
| 2021/0186990 A1 | 6/2021 | Cohen et al. |
| 2021/0244637 A1 | 8/2021 | Shchepinov |
| 2021/0251933 A1 | 8/2021 | Shchepinov |
| 2022/0009950 A1 | 1/2022 | Shchepinov |

FOREIGN PATENT DOCUMENTS

| | | |
|---|---|---|
| EP | 1548116 A1 | 6/2005 |
| EP | 1834639 A1 | 9/2007 |
| EP | 1961311 A1 | 8/2008 |
| EP | 2641891 A1 | 9/2013 |
| FR | 2721518 A3 | 12/1995 |
| JP | H02237919 A | 9/1990 |
| JP | H08268885 A | 10/1996 |
| JP | H09143492 A | 6/1997 |
| JP | H10291955 A | 11/1998 |
| JP | 2000290291 A | 10/2000 |
| JP | 2001145880 A | 5/2001 |
| JP | 2001514239 A | 9/2001 |
| JP | 2001270832 A | 10/2001 |
| JP | 2001519355 A | 10/2001 |
| JP | 2002513911 A | 5/2002 |
| JP | 2002527387 A | 8/2002 |
| JP | 2002536981 A | 11/2002 |
| JP | 2004081156 A | 3/2004 |
| JP | 2004520848 A | 7/2004 |
| JP | 2004530635 A | 10/2004 |
| JP | 2005510501 A | 4/2005 |
| JP | 2006502081 A | 1/2006 |
| JP | 2006504701 A | 2/2006 |
| JP | 2006510669 A | 3/2006 |
| JP | 2008504372 A | 2/2008 |
| JP | 2009007337 A | 1/2009 |
| JP | 2009502745 A | 1/2009 |
| JP | 2009525948 A | 7/2009 |
| JP | 2010521493 A | 6/2010 |
| JP | 2013509439 A | 3/2013 |
| JP | 2013189437 A | 9/2013 |
| JP | 2014502974 A | 2/2014 |
| JP | 2016138138 A | 8/2016 |
| KR | 20050029582 A | 3/2005 |
| WO | 9956790 A2 | 11/1999 |
| WO | 0021524 A1 | 4/2000 |
| WO | 0117374 A1 | 3/2001 |
| WO | 02096221 A2 | 12/2002 |
| WO | 03035095 A1 | 5/2003 |
| WO | 03051348 A2 | 6/2003 |
| WO | 03064576 A2 | 8/2003 |
| WO | 2004028536 A1 | 4/2004 |
| WO | 2004029254 A1 | 4/2004 |
| WO | 2004052227 A2 | 6/2004 |
| WO | 2005037848 A2 | 4/2005 |
| WO | 2007049098 A2 | 5/2007 |
| WO | 2007102030 A1 | 9/2007 |
| WO | 2008143642 A2 | 11/2008 |
| WO | 2009017833 A2 | 2/2009 |
| WO | 2009097331 A1 | 8/2009 |
| WO | 2009114809 A1 | 9/2009 |
| WO | 2009114814 A2 | 9/2009 |
| WO | 2009123316 A1 | 10/2009 |
| WO | 2009151125 A1 | 12/2009 |
| WO | 2010010365 A1 | 1/2010 |
| WO | 2010014585 A1 | 2/2010 |
| WO | 2010068867 A1 | 6/2010 |
| WO | 2010106211 A1 | 9/2010 |
| WO | 2010132347 A2 | 11/2010 |
| WO | 2010143053 A1 | 12/2010 |
| WO | 2011053870 A1 | 5/2011 |
| WO | 2011097273 A1 | 8/2011 |
| WO | 2012100347 A1 | 8/2012 |
| WO | 2012148926 A2 | 11/2012 |
| WO | 2012148927 A2 | 11/2012 |
| WO | 2012148929 A2 | 11/2012 |
| WO | 2012148930 A2 | 11/2012 |
| WO | 2012174262 A2 | 12/2012 |
| WO | 2017037567 A1 | 3/2017 |
| WO | 2017062992 A1 | 4/2017 |
| WO | 2017091279 A1 | 6/2017 |
| WO | 2018094116 A1 | 5/2018 |
| WO | 2019/204582 A1 | 10/2019 |
| WO | 2019195467 A1 | 10/2019 |
| WO | 2019241746 A1 | 12/2019 |
| WO | 2021163186 A1 | 8/2021 |
| WO | 2021163580 A1 | 8/2021 |
| WO | 2022170134 A2 | 8/2022 |
| WO | 2023023397 A1 | 2/2023 |

OTHER PUBLICATIONS

Non-Final Office Action issued in U.S. Appl. No. 16/997,692, mailed on Feb. 4, 2022.

Brenna, J. Thomas et al. (2020, e-published Aug. 29, 2020). "Plasma and Red Blood Cell Membrane Accretion and Pharmacokinetics of RTOO1 (bis-Allylic 11, 11-D2-Linoleic Acid Ethyl Ester) during Long Term Dosing in Patients." Journal of Pharmaceutical Sciences, 109(11), 3496-3503. https://doi.org/1O.1O16/j.xphs.2O2O.O8.O19.

International Search Report, PCT/US 22/15366, filed on Feb. 4, 2022, date of mailing of the ISR Jul. 1, 2022.

Johnson et al, Potential role of dietary n-3 fatty acids in the prevention of dementia and macular degeneration. The American Journal of Clinical Nutrition 83(6):S1494-1498S (2006).

Journal of Biliary Tract & Pancreas 26(4):351-357 (2005).

Kelland et al; Stereochemistry of Lysine Formation by meso-Diaminopimelate Decarboxylase from Wheat Germ: Use of 1H-13C NMR Shift Correlation to Detect Stereospecific Deuterium Labeling. Biochemistry 24(13):3263-2367 (1985).

(56) References Cited

OTHER PUBLICATIONS

Kelly et al; Assessing the authenticity of single seed vegetable oils using fatty acid stable carbon isotope ratios (13C/12C). Food Chemistry 59(2):181-186 (1997).
King et al: Mitochondria-derived reactive oxygen species mediate blue light-induced death of retinal pigment epithelial cells. Photochem Photobiol. 79(5):470-475 (2004).
Kishore et al; Partial 13C Isotopic Enrichment of Nucleoside Monophosphates: Useful Reporters for NMR Structural Studies. Nucleic Acids Research 33(18):e164 (2005).
Knapp et al; Temperature-dependent isotope effects in soybean lipoxygenase-I : Correlating hydrogen tunneling with protein dynamics. JACS Articles; J. Am. Chem. Soc. 124:3865-3874 (2002).
Knez el al. (Jun. 2015) "Correlates of Peripheral Blood Mitochondrial DNA copy number in a general population", Journal of Hypertension, 33(1): e2.
Kushner et al; Pharmacological uses and perspectives of heavy water and deuterated compounds. Canadian Journal of Physiology and Pharmacology 77:79-88 (1999).
Lambert D. Rationale and applications of lipids as prodrug carriers. European Journal of Pharmaceutical Sciences. 11(Suppl.2):S15-S27 (2000).
Larson et al. (Aug. 26, 2005) "Disruption of the Coenzyme Binding Site and Dimer Interface Revealed in the 19 Crystal Structure of Mitochondrial Aldehyde Dehydrogenase "Asian" Variant" The Journal of Biological Chemistry, 280:(34) :30550-30556.
Lee et al., (Dec. 12, 2018) "The Interface Between ER and Mitochondria: Molecular Compositions and Functions.", Molecules and Cells, 41(12):1000-1007.
Lefkowitz et al; Where Does the Developing Brain Obtain Its Docosahexaenoic Acid? Relative Contributions of Dietary a-Linolenic Acid, Docosahexaenoic Acid, and Body Stores in the Developing Rat. Pediatric Research 57 (1):157-165 (2005).
Lei et al.: Dietary omega-3 Polyunsaturated Fatty Acids Enhance Adiponectin Expression and Protect Against Pressure Overload-Induced Left Ventricular Hypertrophy and Dysfunction. Journal of Cardial Failure, Churchill Livingstone, Naperville, IL, US 13(6):S79 (2007).
Levenson et al; The Healing of Rat Skin Wounds. Annals of Surgery 161(2):293-308 (1965).
Li et al. (Feb. 2006) "Mitochondrial Aldehyde Dehydrogenase-2 {ALDH2) Glu504Lys Polymorphism Contributes to the Variation in Efficacy of Sublingual Nitroglycerin" The Journal of Clinical Investigation, 116:506-511.
Lichtenstein et al; Comparison of deuterated leucine, valine and lysine in the measurement of human apolipoprotein A-I and B-100 kinetics. Journal of Lipid Research 31(9):1693-1702 (1990).
Lin et al. (Oct. 2006) "Mitochondrial dysfunction and oxidative stress in neurodegenerative diseases", Nature, 443: 787-795.
Lin et al; Whole body distribution of deuterated linoleic and a-linolenic acids and their metabolites in the rat. Journal of Lipid Research 48:2709-2724 (2007).
Liu et al, (Mar. 15, 2005) "Alzheimer-Specific Epitopes Of Tau Represent Lipid Peroxidation-Induced Conformations", Free Radical Biology and Medicine, 38(6):746-754.
Liuzzi et al.: Inhibitory effect of polyunsaturated fatty acids on MMP-9 release from microglial cells—implications for complementary multiple sclerosis treatment. Neurochem. Res. 32:2184-2193 (2007).
Mantena et al.: Mitochondrial dysfunction and oxidative stress in the pathogenesis of alcohol- and obesity-induced fatty liver diseases. Free Radical Biology & Medicine 44(7):1259-1272 (2008).
Marchitti et al. (Jun. 2007) "Neurotoxicity and Metabolism of the Catecholamine-Derived 3,4-dihydroxyphenylacetaldehyde and 3,4-Dihydroxyphenylglycolaldehyde: The Role of Aldehyde Dehydrogenase" Pharmacological Reviews, 59(2):125-150.
Marchitti et al. (Jun. 2008) "Non-P450 Aldehyde Oxidizing Enzymes: The Aldehyde Dehydrogenase Superfamily" Expert Opinion on Drug Metabolism & Toxicology, 4(6):697-720(37 pages).

Mattson et al. (Dec. 10, 2008) "Mitochondria in Neuroplasticity and Neurological Disorders", Neuron, 60(5):748-766 (36 Pages.
Mazza et al, Omega-3 fatty acids and antioxidants in neurological and psychiatric diseases: An overview. Progress in Neuro-Psychopharmacology & Biological Psychiatry, Oxford 31(1):12-26 (2007).
McClements et al. {Oct. 2007) "Emulsion-Based Delivery Systems for Lipophilic Bioactive Components" Journal of Food Science, 72(8):R109-R124.
Mitsumoto et al.: Oxidative stress biomarkers in sporadic ALS Amyotroph Lateral Scler. 9(3):177-183 (2008).
Morris MC. The role of nutrition in Alzheimer's disease: epidemiological evidence. Eur J Neural. 2009; 16(Suppl 1): 1-7.
Murphy et al. (1999) "Mitochondria in Neurodegeneration: Bioenergetic Function in Cell Life and Death", Journal of Cerebral Blood Flow and Metabolism, 19(3): 231-245.
Nass et al; Caenorhabditis elegans in Parkinson's Disease Drug Discovery: Addressing an Unmet Medical Need; Molecular Interventions 8(6):284-293 (2008).
Nelson et al.: Reduction of beta-Amyloid Levels by Novel Protein Kinase C epsilon Activators. Journal of Biological Chemistry 284(50):34514-34521 (2009).
Nema et al. May 9-Jun. 2011. "Excipients and their Role in Approved Injectable Products: Current Usage and Future Directions" PDA Journal of Pharmaceutical Science and Technology, 65(3):287-332.
Niki Etsuo (2015) "Lipid Oxidation in the Skin", Free Radical Research, 49(7}:827-834 (34 pages).
Non-Final Office Action issued in U.S. Appl. No. 16/997,692, mailed on Feb. 4, 2022, 43 pages.
Notice of Reasons for Rejection dated Aug. 24, 2011 for Japanese Patent Application No. 2008-557833.
Oba et al.; A simple rout to L-[5,5,6,6-D4] lysine starting from L-pyroglutamic acid. Japanese Journal of Deuterium Science 12(1):1-5 (2006).
Odetti et al. (May 2000) "Lipoperoxidation Is Selectively Involved in Progressive Supranuclear Palsy", Journal of Neuropathology & Experimental Neurology, 59(5): 393-397.
Office Action dated Apr. 13, 2018 for Canadian Application No. 2,834,274.
Office Action for Japanese Patent Application No. 2014-508486 mailed on Dec. 25, 2015.
Office Action for Japanese Patent Application No. 2014-508487 mailed on Dec. 3, 2015.
Office Action for Japanese Patent Application No. 2014-508488 mailed on Dec. 4, 2015.
Office Action for Japanese Patent Application No. 2014-508489 mailed on Dec. 25, 2015.
Office Action for U.S. Appl. No. 12/916,347 mailed on Sep. 30, 2016.
Office Action for U.S. Appl. No. 14/113,546 mailed on Feb. 22, 2016.
Office Action for U.S. Appl. No. 14/113,546 mailed on Jan. 16, 2015.
Office Action for U.S. Appl. No. 14/113,546 mailed on Jul. 2, 2015.
Office Action for U.S. Appl. No. 14/113,546 mailed on Sep. 16, 2014.
Office Action for U.S. Appl. No. 14/113,547 mailed on Feb. 19, 2016.
Office Action for U.S. Appl. No. 14/113,547 mailed on Jan. 16, 2015.
The Aldrich Catalog Handbook of Fine Chemicals 2003-2004, p. 140, catalog No. 48, 998-0 (2003-2004).
U.S. Appl. No. 12/916,347 Office Action dated Jul. 12, 2013.
U.S. Appl. No. 12/916,347 Office Action dated Nov. 20, 2017.
U.S. Appl. No. 12/916,347 Office Action dated Oct. 22, 2015.
U.S. Appl. No. 16/103,343 Office Action dated Jan. 3, 2020.
U.S. Appl. No. 16/997,692 Notice of Allowance dated Jun. 8, 2022.
U.S. Appl. No. 16/997,692 Office Action dated Feb. 4, 2022.
Urtti A. Challenges and obstacles of ocular pharmacokinetics and drug delivery, Advanced Drug Delivery Reviews, 2006;58:1131-1135.

(56) References Cited

OTHER PUBLICATIONS

Veldink et al.: Intake of polyunsaturated fatty acids and vitamin E reduces the risk of developing amyotrophic lateral sclerosis. J Neuro Neurosurg. Psychiatry 78(4):367-371 (2007).
Viswanathan and Cushley, Deuterium Nuclear Magnetic Resonance Study of the Interaction of Substrates and Inhibitors with Soybean Lipoxygenase. The Journal of Biological Chemistry 256(14):7155-7160 (1981).
Wade, David; Deuterium isotope effects on noncovalent interactions between molecules. Chemico-Biological Interactions 117(3):191-217 (1999).
Wendt et al.: Mass spectrometry of perdeuterated molecules of biological origin fatty acid esters from Scenedesmus obliquus. Biochemistry 9(25):4854-4866 (1970).
Wey et al. (Feb. 2012) "Neurodegeneration and Motor Dysfunction in Mice Lacking Cytosolic and Mitochondrial Aldehyde Dehydrogenases: Implications for Parkinson's Disease" PLoS One, 7(2):e31522 (11 pages).
Wheeler et al.: The Synthesis of the 2H, 3H, and 14C-Isotopomers of 2'-Deoxy-2', 2'-Difourocytidine Hydrochloride, and Anti-Tumor Compound; Journal of Labelled Compounds and Radiopharmaceuticals 29(5):583-589 (1991).
Wilczynska-Kwiatek A et al.: Asthma, allergy, mood disorders, and nutrition. European Journal of Medical research, Biomed Central Ltd. London, UK 14(Suppl 4):248-254 (2009).
Written Opinion dated Sep. 8, 2008 for PCT/GB2007/050112.
Yamauchi et al.: Observation of the Pathway from Lysine to Isoprenoidal Lipid of Halophilic Archaea, Halobacterium halobium and Natrinema pallidum, Using Regiospecifically Deuterated Lysine. Bull. Chem. Soc. Jpn. 74:2199-2205 (2001).
Yashodhara et al., Omega-3 fatty acids: a comprehensive review of their role in health and disease. Postgrad Med J. 85: 84-90 (2009).
Yoneya, et al.: Genetic polymorphisms as risk factors for coronary artery disease. Japanese Journal of Clinical Medicine 56(10):51-56; 2509-2514 (1998).
Yu et al. (Nov. 2009) "Characteristics of Aldehyde Dehydrogenase 2 (Aldh2) Knockout Mice" Toxicology Mechanisms and Methods, 19(9):535-540.
Zarkovic Kamelija (Aug.-Oct. 2003) "4-Hydroxynonenal and Neurodegenerative Diseases", Molecular Aspects of Medicine, 24(4-5): 293-303.
Zesiewicz et al.: Randomized, Clinical Trial of RT001: Early Signals of Efficacy in Friedreich's Ataxia, Published online Apr. 6, 2018 in Wiley Online Library (wileyonlinelibrary.com). Mov Disord. 33(6):1000-1005 DOI: 10.1002/mds.27353 (2018).
Zhang et al. (Oct. 22, 2015) "Impact of Lipid Content on the Ability of Excipient Emulsions to Increase Carotenoid Bioaccessibility from Natural Sources (Raw and Cooked Carrots)" Food Biophysics, 11 :71-80.
Zorova et al (Jul. 1, 2018) "Mitochondrial Membrane Potential", Anal Biochem, 552: 50-59 (23 Pages).
Adams et al.: Case Report: Expanded Access Treatment of an Infantile Neuroaxonal Dystrophy (INAD) Patient with a Novel, Stabilized Polyunsaturated Fatty Acid Drug, American Academy of Neurology conference, poster session, Apr. 2018.
Adhikary et al.: UVA-visible photo-excitation of guanine radical cations produces sugar radicals in DNA and model structures. Nucleic Acids Research 33(17):5553-5564 (2005).
Angelova el al. (Mar. 2018) "Role of Mitochondrial ROS in the Brain: From Physiology to Neurodegeneralion", FEBS Letters, 592:692-702.
Angulo et al.: Non-alcoholic fatty liver disease. Journal of Gastroenterology and Hepatology 17 Suppl.:S186-190 (2002).
Anonymous,(Oct. 3, 2016) "A First in Human Study of RT001 in Patients With Friedreich's Ataxia", ClinicalTrials.gov archive, https://clinicaltrials.gov/ct2/show/NCT02445794.
Arun et al., (2016)"Mitochondrial Biology and Neurological Diseases", Current Neuropharmacology, 14(2):143-154.
Asada et al; Stereochemistry of meso-a,e Diaminopimelate Decarboxylase Reaction: The First Evidence for Pyriodoxal 5'-Phosphate Dependant Decarboxylation with Inversion of Configuration. Biochemistry 20(24):6881-6886 (1981).
Aufschnalter el al. (Jan. 2017) "Mitochondrial Lipids In Neurodegeneration". Cell and Tissue Research, 367(1):125-140.
Australian Government, IP Australia, Examination Report No. 2 for Standard Patent Application, dated May 5, 2017, for Application No. 2012249917.
Australian Government, IP Australia, Notice of Acceptance for Patent Application, dated Jun. 6, 2017 for Application No. 2012249917.
Bada et al; Isotopic Fractionation During Peptide Bond Hydrolysis. Geochimica et Cosmoschimica Acta 53:3337-3341 (1989).
Balasubramanian et al; DNA strand breaking by the hydroxyl radical is governed by the accessible surface areas of the hydrogen atoms of the DNA backbone. Proc. Natl. Acad. Sci. USA 95:9738-9743 (1998).
Barber et al: Oxidative stress in ALS: a mechanism of neurodegeneration and a therapeutic target. Biochimica et Biophysica Acta 1762:1051-1067 (2006).
Berkers et al. "Topically Applied Ceramides Interact with the Stratum Corneum Lipid Matrix in Compromised Ex Vivo Skin" Pharm Res (2018) 35:48.
Berkers et al. (Jan. 2017) "Topically Applied Fatty Acids are Elongated before Incorporation In the Stratum Comeum Lipid Matrix in Compromised Skin", Experimental Dermatology, 26(1 ):36-43 20 pages.
Berkowitz et al. (Feb. 2016) "MRI of Retinal Free Radical Production With Laminar Resolution In Vivo" Investigative Ophthalmology & Visual Science, 57(2):577-585.
Berkowitz et al_ (Dec. 2015) "Measuring In Vivo Free Radical Production by the Outer Retina" Investigative Ophthalmology & Visual Science, 56:7931-7938.
Bieschke et al. Small Molecule Oxidation Products Trigger Disease-Associated Protein Misfolding. Acc. Chem. Res. 2006;39:611-619.
Brandl et al; The biosynthesis of 3-(trans-2-Nitrocyclopropyl)alanine, a Constituent of the Signal Metabolite Hormaomycin. European Journal of Organic Chemistry 2005(1):123-135 (2004).
Brenna et al. (Nov. 2020) "Plasma and Red Blood Cell Membrane Accretion and Pharmacokinetics of RT001 2 bis-Allylic 11, 11-02-Linoleic Acid Ethyl Ester) during Long Term Dosing in Patients", Journal of Pharmaceutical Sciences, 109(11):3496-3503.
Brenna et al; a-Linolenic acid supplementation and conversionton to n-3 long-chain polyunsaturated fatty acids in humans. Prostaglandins, Leukotrienes and Essential Fatty Acids 80:85-91 (2009).
Brenna et al; High-Precision Continuous-Flow Isotope Ratio Mass Spectrometry. Mass Spectrometry Review 16:227-258 (1997).
Brenna, J.T .; Efficiency of conversion of a-linolenic acid to long chain n-3 fatty acids in man. Lipid Metabolism. Curr Opin Clin Nutr Metab Care 5(2):127-132 (2002).
Brenna, J.T.; Use of stable isotopes to study fatty acid and lipoprotein metabolism in man. Prostaglandins, Leukotrienes and Essential Fatty Acids 57(4 & 5):467-472 (1997).
Buee et al. (1999) "Comparative Biochemistry of Tau in Progressive Supranuclear Palsy, Corticobasal Degeneration, FTDP-17 and Pick's Disease", Brain pathology, 9(4): 681-693.
Burdzy et al; Synthesis of stable-isotope enriched 5-methylpyrimidines and their use as probes of base reactivity in DNA. Nucleic Acids Research 30(18):4068-4074 (2002).
Chen et al.: One-Pot Selective Deuteriation of 5'-Dimethoxytritylated Deoxynucleotide Derivatives. Bioorgainc & Medicinal Chemistry Letters 4(6):789-794 (1994).
Chiriac et al; Synthesis of [1,3,6,7-15N, 8-13C] adenine. Journal of Labelled Compounds and Radiopharmaceuticals 42(4):377-385 (1999).
Cho et al; Cooperativity and anti-cooperativity between ligand binding and the dimerization of ristocetin A: asymmetry of a homodimer complex and implications for signal transduction. Chemistry & Biology 3(3):207-215 (1996).
Christy et al. "Single amino acid polymorphism in aldehyde dehydrogenase gene superfamily," Frontiers in Bioscience, Landmark, 2015, vol. 20, pp. 335-376 (Year: 2015).
Cicalese. Hepatocellular carcinoma. Medscape Reference. 2014;1-5 (2014).
Clarke et al.: Isotope-reinforced polyunsaturated fatty acids protect yeast cells from oxidative stress. FASEB J. 24:849.2 (2010).

(56) References Cited

OTHER PUBLICATIONS

Cotticeli et al. (Jul. 19, 2013) "Insights Into The Role of Oxidative Stress in the Pathology of Friedreich Ataxia Using Peroxidation Resistant Polyunsaturated Fatty Acids", Redox Biology, 1: 398-404.
Crombie et al, Synthesis of [14,14-2H2]-linolenic acid and its use to confirm the pathway to 12-oxophytodienoic acid (12-oxoPDA) in plants: a conspectus of the epoxycarbonium ion derived family of metabolites from linoleic and linolenic acid hydroperoxides. Journal of the Chemical Society, Perkin Transactions 1(3):581-587 (1991).
Dalle-Donne et al; Protein carbonylation in human diseases. Trends in Molecular Medicine 9(4):169-176 (2003).
Demidov, V.; Heavy isotopes to avert ageing? Trends in Biotechnology 25(9):371-375 (2007).
Dentistry Dictionary reduced-size edition. Oct. 10, 1989, the first edition, p. 2216-2217 (1989).
Dimauro et al: Mitochondrial respiratory-chain diseases. N Engl J Med. 348(26):2656-2668 (2003).
D'Souza et al_ (Apr. 2015) "Characterization of Aldh2-/-Mice as an Age-related Model of Cognitive Impairment and Alzheimer's Disease" Molecular Brain, 8(27): 16 pages.
Duncan et al.: A nonsense mutation in COQ9 causes autosomal-recessive neonatal-onset primary coenzyme Q10 deficiency: a potentially treatable form of mitochondrial disease. The American Journal of Human Genetics 84:558-566 (2009).
Dyall et al. Neurological benefits of Omega-3 Fatty Acids. Neuromolecular Medicine 10(4):219-235 (2008).
Eiyo Hyoka-to Chiryo [Nutritional assessment and treatment], 2004, vol. 21, No. 3, p. 41 (247)-46(252).
Elharram et al.: Deuterium-reinforced polyunsaturated fatty acids improve cognition in a mouse model of sporadic Alzheimer's disease. The FEBS Journal 284(23):4083-4095 (2017).
Emken et al; Effect of Dietary Docosahexaenoic Acid on Desaturation and Uptake in vivo of Isotope-Labeled Oleic, Linoleic, and Linolenic Acids by Male Subjects. Lipids 34(8):785-791 (1999).
Emken et al; Metabolism of cis-12-octadecenoic acid and trans-9, trans- 12-octadecadienoic acid and their influence on lipogenic enzyme activities in mouse liver. Biochimica et Biophysica Acta 919:111-121 (1987).
Esaki et al; Synthesis of base-selectively deuterium-labelled nucleosides by the Pd/C-Catalyzed H-D Exchange Reaction in Deuterium Oxide. Heterocycles 66:361-369 (2005).
Esteras et al. (Sep. 21, 2020} "Mitochondrial Calcium Deregulation in the Mechanism of Beta-Amyloid and Tau Pathology", Cells, 9{2135): 1-17.
Evans et al, Endor, triple resonance and ESR studies of spin-trapped radicals in autoxidized linoleic acid and its deuterated derivatives. Biochimica et Biophysica Acta, Elsevier Science BV, Amsterdam, NL 835(3):421-425 (1985).
Extended European Search Report dated Jul. 12, 2011 for EP Application No. 09721095.9.
Extended European Search Report for European Application No. 12776294.6 issued on Sep. 25, 2014 by European Patent Office.
Office Action for U.S. Appl. No. 14/113,547 mailed on Jul. 2, 2015.
Office Action for U.S. Appl. No. 14/113,547 mailed on Sep. 16, 2014.
Office Action for U.S. Appl. No. 14/113,553 mailed on Dec. 23, 2014.
Office Action for U.S. Appl. No. 14/113,553 mailed on Jul. 13, 2015.
Office Action for U.S. Appl. No. 14/113,553 mailed on Jun. 2, 2016.
Office Action for U.S. Appl. No. 14/551,450 mailed on Apr. 15, 2015 by U.S. Patent and Trademark Office.
Ovide-Bordeaux et al.: Docosahexaenoic acid affects insulin deficiency- and insulin resistance-induced alterations In cardiac mitochondria. Am J Physiol Regul Interg Comp Physiol 286:R519-R527 (2004).
Pedersen et al.: Protein modification by the lipid peroxidation product 4-hydroxynonenal in the spinal cords of amyotrophic lateral sclerosis patients. Annals of Neurology 44(5):819-824 (1998).
Peng et al.: Structural characterization of a pentadienyl radical intermediate formed during catalysis by prostaglandin H synthase-2. J Am Chem Soc. 123(15):3609-3610 (2001).
Porter et al. (Mar. 2007) "Lipids and Lipid-based Formulations: Optimizing the Oral Delivery of Lipophilic Drugs" Nature Reviews Drug Discovery, 6(3):231-248.
Porter NA., (1984) "Chemistry of Lipid Peroxidation", Methods Enzymol, 105:273-282.
Puente-Maestu et al. (Nov. 20, 2010) "Effects of exercise on mitochondrial DNA content in skeletal muscle of patients with COPD", Thorax, 66(2):121-127.
Raap et al; Enantioseletive syntheses of isotopically labeled a-amino acids. Preparation of (c-13C)-L-a-aminoadipic acid and five isotopomers of L-lysine with 13C, 15N, and 2H in the b-and c-positions. Recueil de Travaux Chimiques de Pays-Bas 109(4):277-286 (1990).
Raefsky et al. (2018) "Deuterated Polyunsaturated Fatty Adds Reduce Brain Lipid Peroxidation and Hippocampal Amyloid B-Peptide Levels, Without Discernable Behavioral Effects in an APP/PS 1 Mutant Transgenic Mouse Model Of Alzheimer's Disease". Neurobiology of aging, 66:165-176 (31 Pages).
Rapoport et al; Delivery and turnover of plasma-derived essential PUFAs in mammalian brain. Journal of Lipid Research 42:678-685 (2001).
Reddy P. H., Mitochondrial medicine for aging and neurodegenerative diseases. Neuromolecular Med. 10(4):291-315 (2008).
Ren et al; Simultaneous metabolic labeling of cells with multiple amino acids: localization and dynamics of histone acetylation and methylation. Proteomics: Clinical Applications 1(1):130-142 (2007).
Riediger et al: A Systemic Review of the Roles of n-3 Fatty Acids in Health and Disease. Journal of the American Dietetic Association 109(4):668-679 (2009).
Rohwedder et al; Measurement of the Metabolic Interconversion of Deuterium-Labeled Fatty Acids by Gas Chromatography/Mass Spectrometry. Lipids 25(7):401-405 (1990).
Rosen et al; Effect of Deuterium Oxide on Wound Healing, Collagen and Metabolism of Rats. New England Journal of Medicine 270(22):1142-1149 (1964).
RT001 in Amyotrophic Lateral Sclerosis, ClinicalTrials.gov NCT04762589, Feb. 21, 2021. 7 pages.
Rustin et al.: Effect of idebenone on cardiomyopathy in Friedreich's ataxia: a preliminary study. Lancet 354 (9177):477-479 (1999).
Salem et al; Arachidonic and docosahexaenoic acids are biosynthesized from their 18-carbon precursors in human Infants. Proc. Natl. Acad. Sci. 93:49-54 (1996).
Scholl et al; Synthesis of 5,5,6,6-D4-L-lystine-aflatoxin B1 for use as a mass spectrometric internal standard. Journal of Labelled Compounds & Radiopharmaceuticals 47(11):807-815 (2004).
Schutt et al: Proteins modified by malondialdehyde, 4-hydroxynonenal, or advanced glycation end products in ipofuscin of human retinal pigment epithelium. Invest Ophthalmol Vis Sci. 44(8):3663-3668 (2003).
Separate Volume/Advances in Medical Science Oxidative Stress Ver.2 Oct. 5, 2006:23-27 (2006).
Serhiyenko V et al.: Simvastatin and Omega-Polyunsaturated Fatty Acids in the Treatment of Cardiomyopathy in Type 2 Diabetes Mellitus Patients. Atherosclerosis Supplements, Elsevier, Amsterdam, NL 9(1):203 (2008).
Shah et al.: Resolving the Role of Lipoxygenases in the Initiation and Execution of Ferroptosis, ACS Cent. ScL 4(3):387-396 (2018).
Shchepinov et al. (2014) "Deuterium Protection of Polyunsaturated Fatty Acids against Lipid Peroxidation: A Novel Approach to Mitigating Mitochondrial Neurological Diseases." Omega-3 Fatty Acids in Brain and Neurological Health, 373-383.
Shchepinov et al. (Aug. 10, 2011) "Isotopic Reinforcement of Essential Polyunsaturated Fatty Acids Diminishes Nigrostriatal Degeneration in a Mouse Model of Parkinson's Disease" Toxicology Letter, 207(2):97-103.
Shchepinov et al. Isotope effect, essential diet components, and prospects of aging retardation. Russian Journal of General Chemistry 80(7):1514-1522 (2010).
Shchepinov et al.: Mitigating effects of oxidation in aging and diseases. Retrotope. 2010; 1-11 (2010).

(56) References Cited

OTHER PUBLICATIONS

Shchepinov, Mikhail; Reactive Oxygen Species, Isotope Effect, Essential Nutrients, and Enhanced Longevity. Rejuvenation Research 10(1):47-59 (2007).
Simpson et al.: Increased lipid peroxidation in sera of ALS patients: a potential biomarker of disease burden. Neurology 62(10):1758-1765 (2004).
Stella et al., Prodrugs: challenges and rewards. vol. 1-2. New York: Published by MPS Press and Springer; 2007.
Sumbalova et al.: Brain energy metabolsms in experimental chronic diabetes: effect of long-term administration of coenzyme 10 and w-3 polyunsaturated fatty acids. Biologia Bratislava 60(17):105-108 (2005).
Supplementary European Search Report & Written Opinion dated Jun. 5, 2013 for EP Application No. 10827578.5.
Svedruzic et al; The Mechanism of Target Base Attack in DNA Cytosine Carbon 5 Methylation. Biochemistry 43 (36):11460-11473 (2004).
Takeshita et al. (Sep. 1994) "Characterization of the Three Genotypes of Low Km Aldehyde Dehydrogenase in a Japanese Population" Human Genetics, 94(3):217-223.
Tamiya et al. Infra-red absorption spectra of deuterated aspartic acids. Spectrochimica Acta 18(7):895-905 (1962).
Tang et al; Kinetic and biochemical analysis of the mechanism of action of lysine 5, 6-aminomutase. Archives of Biochemistry and Biophysics 418(1):49-54 (2003).
The extended European search report for European Patent Application No. 12776313 dated Sep. 17, 2014.
The Journal of the Japanese Society of Internal Medicine, 1992, vol. 81, No. 7, p. 1119(131 )-1124(136).
The Merck Manual, 18th ed., in Japanese, 2006, p. 223,224.
Townend et al.: Dietary Macronutrient Intake and Five-year Incident Cataract: The Blue Mountains Eye Study. American Journal of Ophthalmology, Elsevier, Amsterdam, NL 143(6):932-939 (2007).
Toyama et al; Assignments and hydrogen bond sensitivities of UV resonance Raman bands of the C8-deuterated guanine ring. Journal of Raman Spectroscopy 33(9):699-708 (2002).
Triglycerides. Medium chain triglycerides. Alternative Medicine Review 7(5): 418-420 (2002).
Tucker et al; The synthesis of 11,11-Dideuterolinoleic Acid. Journal of Labelled Compounds 7(1):11-15 (1970).
U.S. Appl. No. 17/169,271, "Methods of Treating Amyotrophic Lateral Sclerosis", filed Feb. 5, 2021, 37 pages.
U.S. Appl. No. 12/916,347 Office Action dated Apr. 6, 2017.
Extended European Search Report for European Application No. 12777440 issued on Sep. 17, 2014 by European Patent Office.
Extended European search report for European Patent Application No. 12776521.2 dated Sep. 17, 2014.
Fahey et al., (Apr. 2007) "How is Disease Progress In Friedreich's Ataxia Best Measured? A Study Of Four Rating Scales", J. Neurol. Neurosurg. Psychiatry, 78(4):411-413.
Finglas et al, Use of an oral/intravenous dual-label stable-isotope protocol to determine folic acid bioavailability from fortified cereal grain foods in women. The Journal of Nutrition 132(5):936-939 (2002).
Firsov et al. (Mar. 2019) "Threshold Protective Effect of Deuterated Polyunsaturated Fatty Acids on Peroxidation of Lipid Bilayers", The FEBS Journal, 286(11 ): 2099-2117.
Fitzmaur!ce et al. Sep. 2003 "Nigral glutathione deficiency is not specific for idiopathic Parkinson's disease", Movement Disorders. 18(9): 969-976.
Fitzmaurice et al. (Dec. 24, 2012) "Aldehyde Dehydrogenase Inhibition as a Pathogenic Mechanism in 5 Parkinson Disease" Proceedings of the National Academy of Sciences of the United States of America, Jan. 8, 2013, e-Published, 110(2):636-641.
Foldesi et al; The Synthesis of Deuterionucleosides; Nucleosides, Nucleotides and Nucleic Acids 19 (10-12):1615-1656 (2000).
Fomich et al: Full library of (bis-allyl)-deuterated arachidonic acids: synthesis and analytical verification. Chemistry Select 1(15):4758-4764 (2016).

Galluzzi et al. (2018) "Molecular Mechanisms of Cell Death: Recommendations of the Nomenclature Committee on Cell Death 2018", Cell Death & Differentiation, 25:486-541.
Ganguly et al., (Mar. 16, 2017) "Proteinopathy, Oxidative Stress And Mitochondrial Dysfunction: Cross Talk In Alzheimer's Disease And Parkinson's Disease", Drug Design, Development and Therapy, 11 :797-810.
Gaschler et al. (2017) "Lipid Peroxidation in Cell Death", Biochemical and Biophysical Research Communications, J82(3 ):419-425.
Geboes et al. Validation of a new test meal for a protein digestion breath test in humans. The Journal of Nutrition 134(4):806-810 (2004).
GenBank (Aug. 1, 1997) "Aldehyde Dehydrogenase 1 [*Homo sapiens*]" Accession No. AAC51652.1, 2 pages.
GenBank (Aug. 4, 2008) "Aldehyde Dehydrogenase 5 Family, Member A 1 [*Homo sapiens*]" Accession No. AAH34321.1, 2 pages.
GenBank (Dec. 7, 2020) "Aldehyde Dehydrogenase, Dimeric NADP-Preferring Isoform 1 [*Mus musculus*]" Accession No. NP_001106196.1, 3 pages.
GenBank (Dec. 12, 2020) "Aldehyde Dehydrogenase X, Mitochondrial Precursor [*Homo sapiens*]" Accession No. NP_000683.3, 3 pages.
GenBank (Feb. 3, 1997) "mp44a12.r1 Barstead MPLRB1 *Mus musculus* cDNA clone IMAGE:572062 5' similar to gb:M31690 Mouse argininosuccinate synthease (MOUSE), mRNA sequence" Accession No. AA105194.1, 2 pages.
GenBank (Feb. 3, 2021) "Aldehyde Dehydrogenase, Mitochondrial Precursor [*Rattus norvegicus*)" Accession No. NP_115792.2, 3 pages.
GenBank (Jan. 18, 2021) "Aldehyde Dehydrogenase, Mitochondrial Isoform 1 Precursor [*Homo sapiens*]" Accession No. NP_000681, 4 Pages.
GenBank (Jan. 18, 2021) "Aldehyde Dehydrogenase, Mitochondrial Isoform 1 Precursor [*Mus musculus*]" Accession No. NP_033786.1, 4 Pages.
GenBank (Jul. 15, 2006) "Aldehyde Dehydrogenase 2 Family (Mitochondrial) [*Homo sapiens*)", Accession No. AAH02967.1, 2 pages.
GenBank (Jul. 23, 1993) "Aldehyde Dehydrogenase Isozyme 3 [*Homo sapiens*)" Accession No. AAB26658.1, 2 pages.
GenBank (Jun. 9, 2008) "Aldehyde Dehydrogenase 3 Family, Member A1 [*Rattus norvegicus*]" Accession No. AAH70924.1, 2 pages.
GenBank (Mar. 18, 2009) "Aldehyde Dehydrogenase 1 Family, Member A1 [*Rattus norvegicus*]", Accession No. AAH61526.1, 2 pages.
Giordano, F. J., Oxygen, oxidative stress, hypoxia, and heart failure. The Journal of Clinical Investigation 115 (3):500-508 (2005).
Gomez-Ramos et a!. (2003} "Effect of the Lipid Peroxidation Product Acrolein on Tau Phosphorylation in Neural Cells", Journal of neuroscience research, 71(6):863-870.
Gould Philip L. (Nov. 1986) "Salt Selection For Basic Drugs". International Journal of Pharmaceutics, 33(1-3):201-217.
Gueraud et al.: Chemistry and biochemistry of lipid peroxidation products. Free Radical Research 44(10):1098-1124 (2010).
Harman, Deham; The Free Radical Theory of Aging. Antioxidants & Redox Signaling 5(5):557-561 (2003).
Harman, Denham; Aging and Oxidative Stress. Journal of International Federation of Clinical Chemistry (JIFCC) 10(1):24-26 (1998).
Hill et al. Isotope-reinforced polyunsaturated fatty acids protect yeast cells from oxidative stress. Free Radical Biology & Medicine 50:130-138 (2011).
Hill et al.: Small amounts of isotope-reinforced polyunsaturated fatty acids suppress lipid autoxidation. Free Radical Biology and Medicine 53:893-906 (2012).
Hulme et al; Chemistry and the Worm: Caenorhabditis elegans as a Platform for Integrating Chemical and Biological Research. Chemical Biology; Angewandte Chemie International Edition 50:4774-4807 (2011).
Hussein, N., Long-chain conversion of [13C] linoleic acid and -linoleic acid in response to marked changes in their dietary intake in men. Journal of Lipid Research 46(2):269-280 (2004).

(56) References Cited

OTHER PUBLICATIONS

Ikeya et al; Evaluation of stereo-array isotope labeling (SAIL) patterns for automated structural analysis of proteins with CYANA. Magnetic Resonance in Chemistry 44:S152-S157 (2006).
Jun. 21, 2022 (WO) International Search Report & Written Opinion PCT/US22/15368.
International Search Report and Written Opinion dated Sep. 10, 2010 for PCT/US2009/037173.
International Search Report and Written Opinion dated Dec. 23, 2010 for PCT/US10/54866.
International Search Report and Written Opinion dated Nov. 29, 2012 for PCT/US2012/034832.
International Search Report and Written Opinion dated Nov. 29, 2012 for PCT/US2012/034833.
International Search Report and Written Opinion dated Nov. 29, 2012 for PCT/US2012/034835.
International Search Report and Written Opinion dated Nov. 29, 2012 for PCT/US2012/034836.
International Search Report and Written Opinion dated Jun. 3, 2009 for PCT/US2009/037161.
International Search Report and Written Opinion PCT/US2022/015366 dated Jul. 1, 2022.
International Search Report and Written Opinion received for Application No. PCT/US2017/062107, mailed on Feb. 13, 2018, 13 pages.
International Search Report and Written Opinion received for PCT Application No. PCT/US2022/015535, mailed on Apr. 18, 2022, 9 pages.
International Search Report dated Jun. 12, 2007 for PCT/GB2007/050112.
Jacquot et al.: Isotope Sensitive Branching and Kinetic Isotope Effects in the Reaction of Deuterated Arachidonic Acids with Human 12- and 15- Lipoxygenases. Biochemistry 47(27):7295-7303 (2008).
Japanese Journal of Clinical Medicine (Separate Volume) Syndrome classified as New Fields Series 13 Liver/Biliary Tract-based Syndrome (second edition) I Liver edition (the first volume) Sep. 20, 2010 p. 196 to 201 (2010).
Powell et al. (Sep. 1998) "Compendium of Excipients for Parenteral Formulations" PDA Journal of Pharmaceutical Science and Technology, 52(5):238-311.

\* cited by examiner

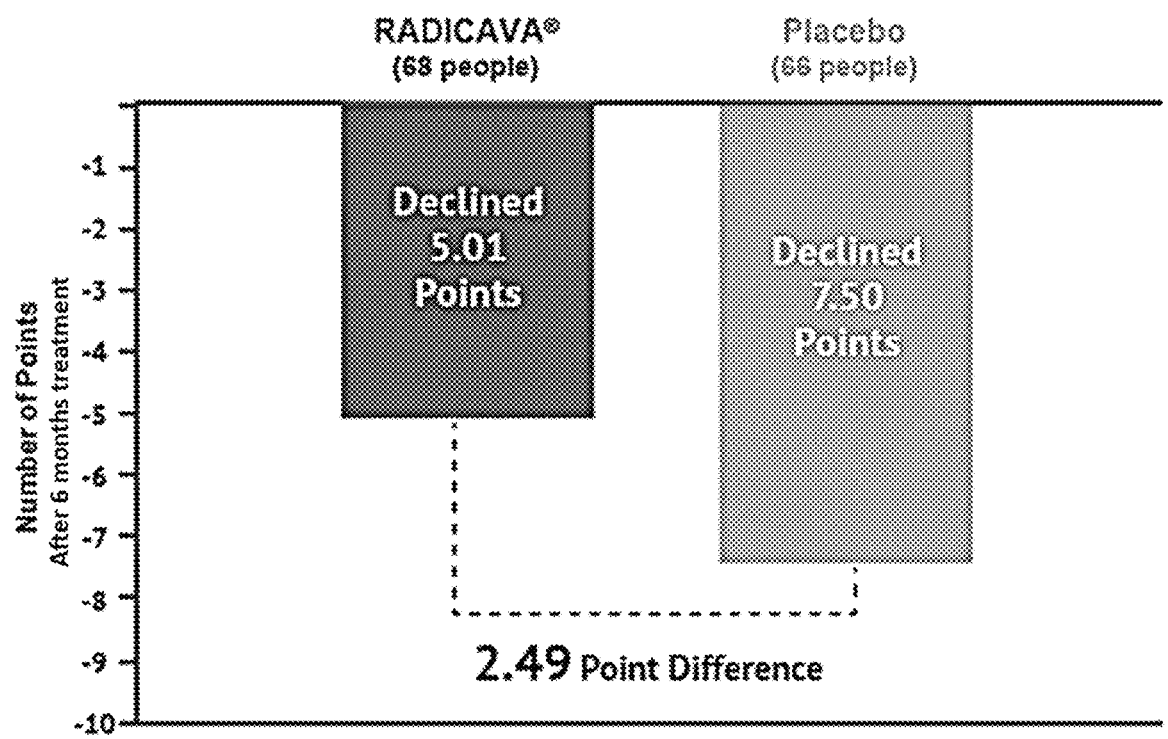

SYNERGISTIC COMBINATION THERAPY FOR TREATING ALS

CROSS-REFERENCE TO RELATED APPLICATIONS

This application claims priority under 35 U.S.C. 119(e) of U.S. Provisional Application Nos. 63/310,541, filed Feb. 15, 2022; 63/310,544, filed Feb. 15, 2022; and is a continuation-in-part of and claims the benefit of U.S. patent application Ser. No. 17/169,271 filed Feb. 5, 2021 and International Patent Application Serial No. PCT/US2022/15366 filed Feb. 4, 2022, all of which are incorporated herein by reference in their entireties.

TECHNICAL FIELD

Disclosed are methods for inhibiting the progression of amyotrophic lateral sclerosis (ALS) in humans. The methods use a synergistic combination of 3-methyl-1-phenyl-2-pyrazoline-5-one (commercially available under the name "edaravone" from Millipore Sigma, St. Louis, Mo., USA, and sold for the treatment of ALS) and a prodrug of deuterated arachidonic acid. When used in combination, edaravone and the prodrug have been shown to significantly reduce the rate of disease progression.

BACKGROUND

ALS is a debilitating and fatal neurodegenerative disease in humans which despite the best efforts of researchers remain incurable. As such, the attending clinician attempts to slow the progression of the disease and maintain the quality of life for the patient for as long as possible.

ALS is a fatal, late-onset, progressive neurological disease with its corresponding pathological hallmarks including progressive muscle weakness, muscle atrophy and spasticity, all of which reflect the degeneration and death of upper or lower motor neurons. Once diagnosed, most patients undergo an initial slower rate of disease progression followed by a rapid rate of progression terminating in death typically within 3 to 4 years, with some patients succumbing even earlier.

The underlying hallmarks of the disease involve lipid auto-peroxidation (LPO) of polyunsaturated fatty acids (PUFAs) in the motor neurons. Central to this oxidative pathway is the presence of labile bis-allylic hydrogen atoms found in arachidonic acid, the dominant PUFA found in neurons. The structure of arachidonic acid including identification of the bis-allylic sites is as follows:

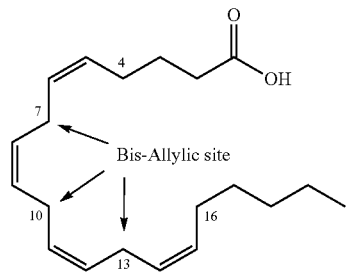 [SMILES: CCCCC/C=C\C/C=C\C/C=C\C/C=C\CCCC(=O)O]

In cellular membranes, arachidonic acids are stacked together and oxidative processes involving reactive oxygen species (ROS) act as an initiator for autoxidation of these PUFAs by extraction of the bis-allylic hydrogen and formation of an oxidative reactive species in the PUFA. Initial oxidation at a first bis-allylic site then leads to serial oxidation of further PUFAs in the membrane of the cell or the mitochondria. The oxidative process starts with hydrogen extraction at a bis-allylic site on the first PUFA and proceeds in a serial manner to the next PUFA and then the next PUFA and so on. At some point the oxidative process damages or destroys the viability of the neuron leading to furtherance of the disease condition that is responsible for generation of the excessive amounts of ROS.

Heretofore, the art has disclosed that an edaravone, an antioxidant and free radical scavenger, provides a reduction in the rate of loss functionality characteristic of ALS. Likewise, the art has disclosed that the progression of ALS can be attenuated by deuteration at one or more of the bis-allylic sites of arachidonic acid found in the neurons. The stability of the deuterium-carbon bond against such oxidative processes is significantly stronger (more stable) than that of the hydrogen-carbon bond including deuterated arachidonic acid comprising two deuteriums substituted at the 13-position (each hydrogen replaced with a deuterium). This means that the generation of oxidative species at the bis-allylic sites is reduced by the carbon-deuterium bonds that the auto-oxidative pathway is inhibited. In turn, termination of this pathway leads to enhanced survival of the neurons and, as such, attenuates the progression of the disease.

As shown in the Examples herein, the unpublished data from a clinical trial evidence that, during the period of rapid decline in functionality associated with ALS, patients treated with a prodrug of a 13,13-D2-arachidonic acid have shown a benefit compared to those not so treated. This benefit was manifested by a reduction in loss of functionality as compared to placebo. While that reduction was meaningful, there remains a need for treatments for ALS where the rate of loss of functionality is even more significant.

SUMMARY

Disclosed are methods for significantly attenuating the progression of ALS by administration of a synergistic combination of edaravone and a deuterated arachidonic acid or a prodrug thereof. Patients treated with such a combination exhibit reductions in the rate of loss of functionality that exceeds that of either drug alone. Indeed, patients treated with both drugs evidenced minimal loss of functionality over the duration of treatment.

Accordingly, in one embodiment, there is provided a method for reducing the rate of ALS disease progression in a patient, which method comprises administering to the patient an effective amount of edaravone or a pharmaceutically acceptable salt thereof in combination with an effective amount of a deuterated arachidonic acid or a prodrug thereof. When so administered, this combination reduces the rate of loss of functionality by more than the additive amount achieved by either drug alone.

In one embodiment, there is provided a method for reducing the rate of loss of functionality in an ALS patient being treated with an effective amount of a deuterated arachidonic acid or a prodrug thereof which method comprises further administering to said patient an effective amount of edaravone or a pharmaceutically acceptable salt thereof. When so administered, this combination reduces the rate of loss of functionality by more than the additive amount achieved by either drug alone.

In one embodiment, there is provided a method for reducing the rate of loss of functionality in an ALS patient being treated with an effective amount of edaravone or a pharmaceutically acceptable salt thereof which method comprises further administering to said patient an effective amount of a deuterated arachidonic acid or a prodrug thereof. When so administered, this combination reduces the rate of loss of functionality by more than the additive amount achieved by either drug alone.

In one embodiment, edaravone or a pharmaceutically acceptable salt thereof is administered in accordance with the product insert for RADICAVA® (edaravone) which insert is incorporated herein by reference in its entirety. The insert can be accessed, for example, at www.radicava.com/assets/dist/pdfs/radicava-prescribing-information.pdf.

In one embodiment, the deuterated arachidonic acid or a prodrug thereof is administered using a dosing regimen that includes a loading dose and a maintenance dose as described herein.

In one embodiment, the prodrug of a deuterated arachidonic acid is 11,11-D2-linoleic acid or an ester thereof. In vivo, a portion of this prodrug is converted to the corresponding 13,13-D2-arachidonic acid which is the active agent in the motor neurons. Generally, it takes several weeks/months to achieve a therapeutic concentration of 13,13-D2-arachidonic acid in the motor neurons by use of this prodrug. However, the use of the loading dose followed by the maintenance dose allows for more uptake of 13,13-D2-arachidonic acid (D2-AA) in the motor neurons, thereby reducing the time from start of therapy to sustained protection against LPO.

In one embodiment, the prodrug of the deuterated arachidonic acid is an ester of 7,7,10,10,13,13-D6-arachidonic acid (D6-AA). The administration of this compound obviates the need for in vivo conversion as is required for 11,11-D2-linoleic acid and provides for a more rapid uptake into the motor neurons coupled with enhanced protection against LPO.

In one embodiment, when the prodrug is 11,11-D2-linoleic acid ethyl ester, it is administered daily at a dose of between about 5.5 and about 12 grams per day or between about 7 and about 12 grams per day, e.g. about 9 grams/day (e.g., 8.64 grams/day) during the loading phase and then at a dose of between 3 and 8 grams per day, e.g. about 5 grams/day (e.g., 4.80 grams/day) or about 6 grams/day (5.76 gram/day) during the maintenance phase provided that the maintenance dose is less than the loading dose.

In one embodiment, edaravone is provided as a formulation sold under the name RADICAVA® by Mitsubishi Tanabe, Osaka, Japan. In one embodiment, edaravone is provided in an orally deliverable form in a water composition as per U.S. Pat. No. 10,987,341 which is incorporated herein by reference in its entirety.

In one embodiment, edaravone is combined with a deuterated arachidonic acid ester prodrug. For example, 11,11-D2-linoleic acid ethyl ester is an oil at room temperature and edaravone is preferably added to the oil and mixed until homogeneous. The recommended dose for edaravone is 60 mg per administration and, accordingly, in one embodiment, this dose is combined with capsules of 11,11-D2-linoleic acid ethyl ester taken daily by the patient. In one embodiment, nine 1-gram pills comprising a total of 8.64 grams of 11,11-D2-linoleic acid ethyl ester (D2-LA ethyl ester) are administered in three 3 pill increments three times a day to the patient.

In one embodiment, edaravone is added to the oil phase of D2-LA ethyl ester. For example, edaravone can be added to three pills comprising D2-LA ethyl ester and appropriately marked to that these pills are taken together. For example, the capsules containing edaravone can be colored differently from those that do not. Alternatively, the 60 mg of edaravone can be divided equally in all 9 pills (i.e., about 6.6 mg per pill). In either case, the two drugs can be mixed together to form a combination that is suitable for oral delivery.

In one embodiment, the prodrug of a deuterated arachidonic acid is 7,7,10,10,13,13-D6-arachidonic acid ethyl ester. Because this compound does not require in vivo conversion as does D2-LA and because only about 10% of D2-LA is converted to D2-AA, the amount of D6-AA ethyl ester required for therapy is about 10% of D2-LA. Still further and as shown in the Examples, D6-AA is shown to be about twice as active than D2-AA albeit in an inflammation model. However, such is considered a good yardstick for the improved activity herein. Accordingly, in some embodiments the amount of D6-AA required for treatment is about 0.05 to about 2 gram per day. In this case, either 1, 2, or 3 capsules can be used to administer D6-AA. In one embodiment, this dose of D6-AA can be administered in one setting with the 60 mg dose of edaravone being included in either 1,2, or 3 of the D6-AA capsules or equally divided in all capsules when such is used.

In one embodiment, there is provided a composition comprising edaravone and a deuterated arachidonic acid or a prodrug thereof. This composition is designed for oral administration, intravenous administration, or administration by infusion.

In one embodiment, said deuterated arachidonic acid prodrug is 11,11-D2-linoleic acid or an ester thereof.

In one embodiment, said deuterated arachidonic acid prodrug is a 7,7,10,10,13,13-D6-arachidonic ester.

In one embodiment, said ester is an ethyl ester.

In one embodiment, there is provide a kit of parts comprising at least one daily dose of edaravone and at least one daily dose of a deuterated arachidonic acid or a prodrug thereof.

BRIEF DESCRIPTION OF THE DRAWING

FIG. 1 provides a correlation between the natural course of ALS with the corresponding loss of functionality versus the loss of functionality for patients on edaravone after 6 months of treatment.

DETAILED DESCRIPTION

Disclosed are methods for inhibiting the progression of amyotrophic lateral sclerosis (ALS) in humans. The methods use a synergistic combination of 3-methyl-1-phenyl-2-pyrazoline-5-one (commercially available under the trademark RADICAVA® and sold for the treatment of ALS) and a prodrug of the deuterated arachidonic acid.

Prior to discussing this invention in more detail, the following terms will first be defined. Terms that are not defined are given their definition in context or are given their medically acceptable definition.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the term "optional" or "optionally" means that the subsequently described event or circumstance can or cannot occur, and that the description includes instances where the event or circumstance occurs and instances where it does not.

As used herein, the term "about" when used before a numerical designation, e.g., temperature, time, amount, concentration, and such other, including a range, indicates approximations which may vary by (+) or (−) 15,% 10%, 5%, 1%, or any subrange or subvalue there between. Preferably, the term "about" when referencing an amount or other feature including a dose amount, means that that amount may vary by +/−10%.

As used herein, the term "comprising" or "comprises" is intended to mean that the compositions and methods include the recited elements, but not excluding others.

As used herein, the term "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

As used herein, the term "consisting of" shall mean excluding more than trace elements of other ingredients and substantial method steps. Embodiments defined by each of these transition terms are within the scope of this invention.

As used herein, the term "edaravone" refers to 3-methyl-1-phenyl-2-pyrazoline-5-one or a salt thereof which can be represented by the formula:

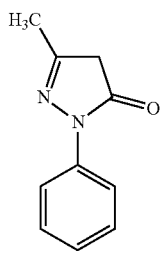

As used herein and unless the context dictates otherwise, the term "deuterated arachidonic acid" refers to arachidonic acid comprising replacement of at least both hydrogen atoms at the 13-position with two deuterium atoms as well as pharmaceutically acceptable salts thereof. Such deuterated arachidonic acids include but are not limited to 13,13-D2-arachidonic acid, 10,10-13,13-D4-arachidonic acid, and 7,7,10,10,13,13-D6-arachidonic acid and salts thereof. As to 7,7,10,10,13,13-D6-arachidonic acid, such compounds can further comprise modest deuteration at the mono-allylic sites (i.e, the 4-position and the 16-position) arising from catalytic synthesis of this deuterated compound as described in U.S. Pat. No. 10,730,821 which is incorporated herein by reference in its entirety. In general, about 40 percent or less of the aggregate of hydrogen atoms at these mono-allylic positions are replaced by deuterium with a higher deuterium load typically found at the 16-position than at the 4-position.

As used herein and unless the context dictates otherwise, the term "a prodrug" as used relative to deuterated arachidonic acid ("drug") refers to compounds which, in vivo, provide for this drug. In one embodiment, the prodrug is an ester of a deuterated arachidonic acid. Such deuterated arachidonic acids include 13,13-D2-arachidonic acid, 10,10-13,13-D4-arachidonic acid, and 7,7,10,10,13,13-D6-arachidonic acid.

In one embodiment, the prodrug can comprise 11,11-D2-linoleic acid or an ester thereof. In vivo, the ester group is removed to provide for 11,11-D2-linoleic acid and a portion of that compound is enzymatically converted to 13,13-D2-arachidonic acid. The non-converted portion of that compound is absorbed into the body and subsequently is used as a source of energy.

In one embodiment, the prodrug can comprise 8,8,11,11-D4-linoleic acid or an ester thereof. In vivo, the ester group is removed to provide for 8,8,11,11-D4-linoleic acid and a portion of that compound is enzymatically converted to 10,10,13,13-D4-arachidonic acid. The non-converted portion of that compound is absorbed into the body and subsequently is used as a source of energy.

In one embodiment, the prodrug is an ester of deuterated arachidonic acid. Such esters include deuterated arachidonic acids such as esters of 13,13-D2-arachidonic acid, 10,10-13,13-D4-arachidonic acid, and 7,7,10,10,13,13-D6-arachidonic acid. As to 7,7,10,10,13,13-D6-arachidonic acid, such compounds can also comprise modest deuteration at the mono-allylic sites (i.e, the 4-position and the 16-position) arising from catalytic synthesis of this compound as described above.

As used herein, the term "linoleic acid" refers to the compound and a pharmaceutically acceptable salt thereof having the formula provided below and having the natural abundance of deuterium (i.e., about 0.0156% naturally occurring deuterium) at each hydrogen atom:

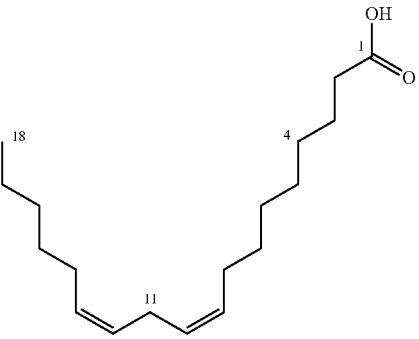 [SMILES: CCCCC/C=C\C/C=C\CCCCCCCC(=O)O]

Esters of linoleic acid or arachidonic acid are formed by replacing the —OH group with an —OR group using methods well known in the art. Such esters are as defined herein below.

As used herein and unless the context dictates otherwise, the term "deuterated linoleic acid or an ester thereof" refers to 11,11-D2-linoleic acid or a $C_1$-$C_6$ alkyl ester, a glycerol ester (including monoglycerides, diglycerides and triglycerides), sucrose esters, phosphate esters (e.g., phospholipids), and the like. The particular ester group employed is not critical provided that the ester group is pharmaceutically acceptable (non-toxic and biocompatible)

As used herein and unless the context dictates otherwise, the term "deuterated arachidonic acid ester" refers to such deuterated arachidonic acids having a $C_1$-$C_6$ alkyl ester, a glycerol ester (including monoglycerides, diglycerides and triglycerides), sucrose esters, phosphate esters (e.g., phospholipids), and the like. The particular ester group employed is not critical provided that the ester group is pharmaceutically acceptable (non-toxic and biocompatible).

As used herein, the term "phospholipid" refers to any and all phospholipids that are components of the cell membrane. Included within this term are phosphatidylcholine, phosphatidylethanolamine, phosphatidylserine, and sphingomyelin. In the motor neurons, the cell membrane is enriched in phospholipids comprising arachidonic acid.

As used herein, the term "pathology of a disease" refers to the cause, development, structural/functional changes, and natural history associated with that disease. The term "natural history" means the progression of the disease in the absence of treatment per the methods described herein.

As used herein, the term "reduced rate of disease progression" means that the rate of disease progression is attenuated after initiation of treatment as compared to the patient's natural history. In one case, the rate of reduction in disease progression using the methods described herein results in a percentage reduction of at least 35% lower or at least 50% lower at a time point, e.g., 3 months to 24 months, e.g., 6 months or 1 year, after initiation of therapy when compared to the natural history of the patient. In ALS, the rate of disease progression is measured by the Revised ALS Functional Rating Scale (ALSFRS-R) which is found at www.mdcalc.com/revised-amyotrophic-lateral-sclerosis-functional-rating-scale-alsfrs-r which is incorporated herein by reference in its entirety. This Rating Scale evaluated 12 different components on a 0 (worse) to 4 (best) scale where the components are speech, salivation, swallowing, handwriting, walking, food handling, dressing and hygiene, turning in bed, walking, climbing stairs, dyspnea, orthopnea, and respiratory insufficiency.

The reduction in the rate of disease progression is confirmed by a reduction in the downward slope (flattening the curve) of a patient's relative muscle functionality during therapy as compared to the downward slope found in the patient's natural history. Typically, the differential between the downward slope measured prior to treatment and the slope measured after at least 90 days from initiation of treatment has a flattening level of at least about 30%. So, a change of 7.5 degrees (e.g., a downward slope of 25 degrees during the natural history that is reduced to a downward slope of 17.5) degrees provides for a 40% decrease in the slope. In any case, the reduction in downward slope evidences that the patient has a reduced rate of disease progression due to the therapy.

As used herein, the term "patient" refers to a human patient or a cohort of human patients suffering from a neurodegenerative disease treatable by administration of a deuterated arachidonic acid or a prodrug thereof.

As used herein, the term "loading or primer amount" refers to an amount of a deuterated linoleic acid or an ester thereof that is sufficient to provide for a reduced rate of disease progression within at least about 45 days after initiation of administration and preferably within about 30 days.

In one embodiment, 11,11-D2-linoleic acid or an ester thereof have been found to be well tolerated by patients with a wide therapeutic window. When a loading dose is employed, it provides for more rapid onset to a steady state concentration of 13,13-D2-arachidonic acid of at least about 12% in red blood cells based on the total amount of arachidonic acid in said cells including the deuterated arachidonic acid, preferably, at least about 15%, and, more preferably, at least about 20%. See, allowed U.S. patent application Ser. No. 17/169,271 which application is incorporated herein by reference in its entirety. Other deuterated arachidonic acid prodrugs are also well tolerated in vivo.

As used herein, the term "maintenance dose" refers to a dose of 11,11-D2-linoleic acid that is less than the primer dose and is sufficient to maintain a therapeutic concentration of 13,13-D2-arachidonic acid in the cell membrane of red blood cells and, hence, in the cell membrane of motor neurons, so as to retain a stable rate of disease progression.

As used herein, the term "periodic dosing" refers to a dosing schedule that substantially comports to the dosing described herein. Stated differently, periodic dosing includes a patient who is compliant at least 75 percent of the time over a 30-day period and preferably at least 80% compliant. In embodiments, the dosing schedule contains a designed pause in dosing. For example, a dosing schedule that provides dosing 6 days a week is one form of periodic dosing. Another example is allowing the patient to pause administration for from about 3 or 7 or more days, e.g., due to personal reasons, provided that the patient is otherwise at least 75 percent compliant.

The term "cohort" refers to a group of at least 2 patients whose results are to be averaged.

As used herein, the term "pharmaceutically acceptable salts" of compounds disclosed herein are within the scope of the methods described herein and include acid or base addition salts which retain the desired pharmacological activity and is not biologically undesirable (e.g., the salt is not unduly toxic, allergenic, or irritating, and is bioavailable). When the compound has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, trimethylamine, pyridine, picoline, ethanolamine, diethanolamine, triethanolamine) or basic amino acids (e.g., arginine, lysine, and ornithine). Such salts can be prepared in situ during isolation and purification of the compounds or by separately reacting the purified compound in its free base or free acid form with a suitable acid or base, respectively, and isolating the salt thus formed.

The phrase "excessive amounts of PUFAs," "excessive PUFA intake," and the like refer to intake of total PUFAs (e.g., total amount of PUFAs consumed per day) that result in reduced conversion of 11,11-D2-linoleic acid to 13,13-D2-arachidonic acid compared to a diet lower in total PUFA intake. In embodiments, the patient is on a diet that restricts intake of linoleic acid, arachidonic acid, and/or other PUFA compounds. The amount of PUFAs that can be consumed by a patient is variable, depending on numerous factors such as the patient's health, weight, age, other medications being taken, liver function, metabolism, and the like.

In general, a patient on a 2,000 calorie per day diet consumes up to about 22 grams of polyunsaturated fatty acids (news.christianacare.org/2013/04/nutrition-numbers-revealed-fat-intake/), of which about 14 grams are linoleic acid when averaged for men and women (www.ncbi.nlm.nih.gov/pmc/articles/PMC3650500/). In addition, only about 10% of the average amount of linoleic acid consumed is hepatically converted to arachidonic acid. So, on average, about 1.4 grams of arachidonic acid is generated per day. When a patient consumes excessive amounts of PUFAs, including linoleic acid, that excess dilutes the effective concentration of 11,11-D2-linoleic acid. In turn, this impacts the amount of 13,13-D2-arachidonic acid that is hepatically generated when all other factors remain constant.

When the amount of total PUFAs consumed is such that the amount of 13,13-D2-arachidonic acid enzymatically generated is less than about 70% per day of that generated when the average amount of PUFAs is consumed, then that patient is considered to have excessive linoleic acid consumption.

Pathology

The discovery of several aldehydes that easily reacted with sulfhydryl groups, resulting in the inhibition of vital metabolic processes, led to the association of polyunsaturated fatty acid peroxidation as a component of the pathology of many of neurodegenerative diseases (Schauenstein, E.; Esterbauer, H. Formation and properties of reactive aldehydes. Ciba Found. Symp. (67):225-244; 1978). Whether as a primary cause of disease or a secondary consequence, such lipid peroxidation is attributed to oxidative stress, which leads to neuronal death, and such is implicated in the progression of ALS.

The oxidative stress responsible for such peroxidation is due to an imbalance between routine production and detoxification of reactive oxygen species ("ROS") that leads to an oxidative attack on the lipid membrane of cells. The lipid membrane as well as the endoplasmic reticulum and mitochondria of motor neurons are highly enriched in arachidonic acid (a 20-carbon chain PUFA having 4 sites of cis-unsaturation). Separating each of these 4 sites are 3 bis-allylic methylene groups. These groups are particularly susceptible to oxidative damage due to ROS, and to enzymes such as cyclooxygenases, cytochromes, and lipoxygenases, as compared to allylic methylene and methylene groups.

Moreover, once a bis-allylic methylene group in one arachidonic acid is oxidized by a ROS, a cascade of further oxidation of other arachidonic acid groups in the lipid membrane occurs. This is because a single ROS generates oxidation of a first arachidonic acid component through a free radical mechanism which, in turn, can oxidize a neighboring arachidonic acid through the same free radical mechanism which yet again can oxidize another neighboring arachidonic acid in a process referred to as lipid chain auto-oxidation. The resulting damage includes a significant number of oxidized arachidonic acid components in the cell membrane.

Oxidized arachidonic acids negatively affect the fluidity and permeability of cell membranes in motor neurons. In addition, they can lead to oxidation of membrane proteins as well as being converted into a large number of highly reactive carbonyl compounds. The latter include reactive species such as acrolein, malonic dialdehyde, glyoxal, methylglyoxal, etc. (Negre-Salvayre A, et al. Brit. J. Pharmacol. 2008; 153:6-20). But the most prominent products of arachidonic acid oxidation are alpha, beta-unsaturated aldehydes such as 4-hydroxynon-2-enal (4-HNE; formed from n-6 PUFAs like LA or AA), and corresponding ketoaldehydes (Esterfbauer H, et al. Free Rad. Biol. Med. 1991; 11:81-128. As noted above, these reactive carbonyls cross-link (bio) molecules through Michael addition or Schiff base formation pathways leading which continues the underlying pathology of the disease.

Disease Progression

When a patient is diagnosed with ALS, the clinician evaluates that patient's rate of disease progression by assessing the patient's loss of functionality in the absence of therapy as described herein. That rate is referred to as the "natural history" of the disease and is typically measured by standardized tests that measure the extent of a patient's functionality over a set period of time. For example, in the case of ALS, there is a standard test referred to as ALSFRS-R which determines the rate of loss of muscle functionality over time and this is used to measure disease progression. This test has 12 components each of which are measured on a 0 (worse) to 4 (best) scale. The ability of a drug to attenuate the rate of disease progression evidences its efficacy. Even a modest reduction in the rate of functionality loss is considered significant.

Heretofore, the treatment of ALS employed deuterated 11,11-D2-linoleic acid or an ester thereof, including those in a lipid bilayer form, has been shown to stabilize polyunsaturated fatty acids against ROS. Examples of such treatments are found in: WO 2011/053870, WO 2012/148946, and WO 2020/102596, each of which is incorporated herein by reference in its entirety.

Each of these documents discloses the in vivo conversion of a portion of 11,11-D2-linoleic acid to 13,13-D2-arachidonic acid which is then incorporated into the motor neurons to stabilize these neurons from oxidative damage. The in vivo accumulation of 13,13-D2-arachidonic acid occurs over months until a therapeutic concentration is achieved. Once a therapeutic concentration of 13,13-D2-arachidonic acids is achieved, continued administration of 11,11-D2-linoleic acid or ester thereof is necessary to maintain such a therapeutic concentration.

Still further, the dosing regimen employed must address the patient's need for rapid onset of therapy, especially given that loss of functionality is typically very quick and quite often well before the end stage of the disease which typically ranges from about 2 to 5 years after diagnosis. Hence, any therapy for treating such neurodegenerative diseases must provide meaningful therapy within a month or less after the start of therapy thereby retaining as much of the patient's functionality as possible and furthermore providing for substantial reductions in the rate of disease progression.

Compound Preparation 11,11-D2-linoleic acid is known in the art and is commercially available. In addition, 11,11-D2-linoleic acid and esters thereof are described, for example, in U.S. Pat. No. 10,052,299 which is incorporated herein by reference in its entirety. Deuterated arachidonic acid esters are also known in the art as provided in U.S. Pat. Nos. 10,577,304 and 10,730,821 each of which is incorporated herein by reference in its entirety.

Methodology—11,11-D2-Linoleic Acid or Ester Thereof

In one of the methods described herein, a patient afflicted with ALS is treated with 11,11-D2-linoleic acid or an ester thereof which is a prodrug for 13,13-D2-arachidonic acid. Upon administration, the 11,11-D2-linoleic acid undergoes in vivo conversion to 13,13-D2-arachidonic acid.

In one embodiment, 11,11-D2-linoleic acid or ester thereof is administered to the patient in sufficient amounts to generate a synergistic concentration in vivo when used in combination with edaravone. In one embodiment, such a synergistic concentration is at least 3% percent 13,13-D2-arachidonic acid in red blood cells based on the total concentration of arachidonic acid including any deuterated arachidonic acid. In a preferred embodiment, sufficient 11,11-D2-linoleic acid or ester thereof is administered to the patient to achieve a steady state concentration of 13,13-D2-arachidonic acid in red blood cells of at least about 12%, preferably, at least about 15% and, more preferably, at least about 20% based on the total amount of arachidonic acid, including deuterated arachidonic acid, found therein.

In one embodiment, deuterated LA or ester thereof is administered to the patient in sufficient amounts to generate a concentration of deuterated AA in red blood cells of at least about 3%, preferably at least 6%, more preferably at least 10%, and most preferably at least 15%, based on the total amount of arachidonic acid, including deuterated arachidonic acid, found therein. At any of these concentrations, the attending clinician can correlate that found concentration to a therapeutic concentration of deuterated AA in the neurons. The percentage of deuterated AA compared to total amount of arachidonic acid in red blood cells, including deuterated AA, may be between about 0.5% and about 60%. In an embodiment, the percentage of deuterated AA compared to total arachidonic acid in red blood cells may be between about 5% and about 50%, between about 10% and about 40%, between about 15% and about 30%, and between about 15% and about 25%. In some embodiments, the dose of deuterated LA is modified (e.g. increased) if the percentage of deuterated AA compared to total amount of arachidonic acid in red blood cells, including deuterated AA, is less than a target amount, e.g., less than about 3%, less than about 6%, less than about 10%, less than about 15%, less than about 20%, less than about 30%, less than about 40%, less than about 50%, or less than about 60%.

In one embodiment, such administration comprises the use of a dosing regimen that includes two dosing components. The first dosing component comprises a primer dose of 11,11-D2-linoleic acid or an ester thereof. The second dosing component comprises a maintenance dose of 11,11-D2-linoleic acid or an ester thereof, wherein the amount of 11,11-D2-linoleic acid or an ester thereof in said second dosing component is less than that in the first dosing component.

As to the primer dose, the amount of 11,11-D2-linoleic acid or an ester thereof employed is designed to provide rapid onset of therapy. Such therapy is measured by a reduction in the disease progression of neurodegenerative diseases as described below. In an embodiment, the primer dose takes into account the various complicating factors, such as the amount of PUFAs consumed by the patient in a given day, the in vivo rate of conversion of 11,11-D2-linoleic acid to 13,13-D2-arachidonic acid, as well as the general turnover rate of lipids (half-life) in the patient's neurons.

Regarding this last point, the lipid components of neurons are not static but, rather, are exchanged over time and have a finite half-life in the body. In general, only a fraction of the lipids components in the lipids are replaced each day. In the case of neurons, these cells are rich in arachidonic acid. The turnover of arachidonic acid in these membranes occurs from a stable pool of lipids comprising arachidonic acid in the spinal fluid. In turn, this stable pool is replaced and replenished over time by arachidonic acid included in the newly consumed lipids by the patient as part of the patient's diet as well as by biosynthesis of arachidonic acid from linoleic acid by the liver. In embodiments, the maintenance dose of the 11,11-D2-linoleic acid is titrated such that the amount converted to 13,13-D2-arachidonic acid is set to at least match the rate of secretion from the body.

The rate of arachidonic acid synthesized in vivo is typically rate limited to the extent that there is a maximum amount of arachidonic acid that the liver can generate in a given day. In turn, only a fraction of the linoleic acid consumed is converted to arachidonic acid with a majority of the linoleic acid remaining unchanged. This limited rate of synthesis of arachidonic acid from linoleic acid results in a delay in such synthesis after administration of the deuterated linoleic acid as the amount of 13,13-D2-arachidonic acid concentration in red blood cells continues to increase after converting from the primer dose to the maintenance dose of the dosing regimen.

Hence, the choice of a dosing of 11,11-D2-linoleic acid or an ester thereof as described herein addresses each of the above components and sets a dosing level that allows for the accumulation of a sufficient amount of 11,11-D2-linoleic acid in the body and, hence, the generation of therapeutic levels of 13,13-D2-arachidonic acid in the red blood cells. When so achieved, the data in the Examples establish that there is a meaningful reduction in the rate of disease progression.

In embodiments, the loading dose of the dosing regimen described herein includes sufficient amounts of 11,11-D2-linoleic acid or an ester thereof that are absorbed into the patient so as to maximize the in vivo conversion of 11,11-D2-linoleic acid 13,13-D2-arachidonic acid. Once maximized, the resulting 13,13-D2-arachidonic acid accumulates in the body until it reaches a therapeutic concentration in the patient. During this process, 13,13-D2-arachidonic acid is systemically absorbed into the cells of the body including neurons, wherein the rate at which such absorption occurs is based on the exchange rate or turnover rate of lipids in the cell membrane of these motor neurons.

In one embodiment, the loading dose comprises about 7 to about 12 grams of 11,11-D2-linoleic acid or ester thereof per day and preferably about 8.64 grams per day of 11,11-D2-linoleic acid ethyl ester (administered 3 capsules, 3 times a day) and a maintenance dose that is less than that of the loading dose—for example, about 5.84 grams of 11,11-D2-linoleic acid (administered 3 capsules, 2 times a day or 2 capsules 3 times a day). In embodiments, daily or periodic dosing of 11,11-D2-linoleic acid or ester thereof in the primer dose ranges from about 5.5 to about 12 grams per day and includes about 5.5 g, about 6 g, about 6.5 g, about 7 g, about 7.5 g, about 8 g, about 8.5 g, about 8.64 g, about 9 g, about 9.5 g, about 10 g, about 10.5 g, about 11 g, about 11.5 g, and about 12 g.

In one embodiment and as evidenced in the examples, a synergistic result using edaravone and 11,11-D2-linoleic acid or ester thereof can be achieved by using as little as about 1.5 grams to about 12 grams of 11,11-D2-linoleic acid or ester thereof. However, the goal of achieving a rapid onset to therapy is best achieved by using the loading dose and maintenance dose as described above.

In an embodiment, the primer or loading dose is continued for at least about 24 days or at least about 45 days, e.g., to rapidly achieve a therapeutic concentration of 11,11-D2-linoleic acid in vivo, thereby reducing the rate of disease progression. In an embodiment, after completion of the primer dose, the maintenance dose is periodically administered. In an embodiment no more than about 70% of the primer dose of 11,11-D2-linoleic acid or an ester thereof per day is administered. Due to its safety profile, the primer or loading dose of D2-LA can be used throughout therapy at the option of the attending clinician.

Methodology—7,7,10,10,13,13-D6-Arachidonic Acid or Ester Thereof

As noted previously, a deuterated arachidonic acid or ester thereof that is administered to the patient includes 7,7,10,10,13,13-D6-arachidonic acid or an ester thereof ("D6-AA") as that term is defined herein. Because the three bis-allylic carbon atoms on these compounds have substantially all of the hydrogens replaced with deuterium, these compounds will provide superior reduction in the reducing or eliminating lipid auto-oxidation. As such, these compounds will provide a meaningful reduction in the rate of progression of ALS. In a preferred embodiment, the D6-AA or ester thereof is delivered in a tiered manner comprising a first and second dosing component. The first dosing component, the primer dose, follows the protocol set forth above with the exception that the primer uses between about 0.05 to about 5 grams or about 0.5 and about 5 grams of D6-AA or an ester thereof daily or periodically. The maintenance dose that is employed is less than the loading dose and is generally between about 30% and about 70% of the loading dose.

In an embodiment, the primer or loading dose is continued for at least about 24 days or at least about 45 days, e.g., to rapidly achieve a therapeutic concentration of 7,7,10,10,13,13-D6-arachidonic acid in vivo, thereby reducing the rate of disease progression. In an embodiment, after completion of the primer dose, the maintenance dose is periodically administered. In an embodiment no more than about 70% of the primer dose of 7,7,10,10,13,13-D6-arachidonic acid or an ester thereof per day is administered. Due to its safety profile, the primer or loading dose of D6-AA can be used throughout therapy at the option of the attending clinician.

The methods described herein administer D6-AA or an ester thereof to a patient in order to accumulate a therapeutic concentration of D6-AA for use in the methods described herein.

In one embodiment, D6-AA or ester thereof is administered to the patient in sufficient amounts to generate a concentration of D6-AA in red blood cells of at least about 3%, preferably at least 6%, more preferably at least 10%, and most preferably at least 15%, based on the total amount of arachidonic acid, including deuterated arachidonic acid, found therein. At any of these concentrations, the attending clinician can correlate that found concentration to a therapeutic concentration of D6-AA in the neurons. The percentage of D6-AA compared to total amount of arachidonic acid in red blood cells, including deuterated AA, may be between about 0.5% and about 60%. In an embodiment, the percentage of D6-AA compared to total arachidonic acid in red blood cells may be between about 5% and about 50%, between about 10% and about 40%, between about 15% and about 30%, and between about 15% and about 25%. In some embodiments, the dose of D6-AA is modified (e.g. increased) if the percentage of D6-AA compared to total amount of arachidonic acid in red blood cells, including deuterated AA, is less than a target amount, e.g., less than about 3%, less than about 6%, less than about 10%, less than about 15%, less than about 20%, less than about 30%, less than about 40%, less than about 50%, or less than about 60%.

In one embodiment, such administration comprises the use of a dosing regimen that includes two dosing components. The first dosing component comprises a primer dose of D6-AA or an ester thereof. The second dosing component comprises a maintenance dose of D6-AA or an ester thereof, wherein the amount of D6-AA or an ester thereof in said second dosing component is less than that in the first dosing component.

As to the primer dose, the amount of D6-AA or an ester thereof employed is designed to provide rapid onset of therapy. Such therapy is measured by a reduction in the disease progression of neurodegenerative diseases as described below. In an embodiment, the primer dose takes into account the various complicating factors, such as the amount of PUFAs consumed by the patient in a given day, as well as the general turnover rate of lipids (half-life) in the patient's neurons.

Regarding this last point, the lipid components of neurons are not static but, rather, are exchanged over time and have a finite half-life in the body. In general, only a fraction of the lipids components in the lipids are replaced each day. In the case of neurons, these cells are rich in arachidonic acid. The turnover of arachidonic acid in these membranes occurs from a stable pool of lipids comprising arachidonic acid in the spinal fluid. In turn, this stable pool is replaced and replenished over time by arachidonic acid included in the newly consumed lipids by the patient as part of the patient's diet as well as by biosynthesis of arachidonic acid from linoleic acid by the liver. In embodiments, the maintenance dose of the D6-AA or ester thereof is titrated such that the amount of D6-AA ester administered matches the rate of secretion of D6-AA from the body.

The methods described herein are also based, in part, on the discovery that when the lipid membrane of neurons is stabilized against LPO, there is a substantial reduction in the progression of the neurodegenerative disease. This is believed to be due to the replacement of hydrogen atoms with deuterium atoms in arachidonic acid, rendering the deuterated arachidonic acid significantly more stable to ROS than the hydrogen atoms. As above, this stability manifests itself in reducing the cascade of lipid auto-oxidation and, hence, limiting the rate of disease progression.

In one embodiment, the methods described herein address this challenge by employing a dosing regimen which delivers D6-AA in amounts sufficient to provide for a therapeutic concentration of deuterated arachidonic acid in the neurons. When so incorporated, the deuterated arachidonic acid reduces the degree of LPO which, in turn, effectively limits progression of ALS provided it is administered in appropriate amounts.

In one of the methods described herein, a patient afflicted with ALS is treated with a D6-AA ester which is a prodrug of D6-AA. Alternatively, D6-AA, including a pharmaceutically acceptable salt thereof, can be administered directly to the patient as the active drug thereof. Upon administration, the D6-AA ester is converted to D6-AA. In either case, this D6-arachidonic acid is readily absorbed by the body.

Methodology—3-methyl-1-phenyl-2-pyrazoline-5-one (edaravone) or a Pharmaceutically Acceptable Salt Thereof Edaravone is commercially available from Millipore Sigma, Inc. and the methods for administering this drug are found on the product insert which is incorporated herein by reference. In one embodiment, edaravone is administered as an infusion such as described in product insert for RADICAVA®, available from Mitsubishi Tanabe, Osaka, Japan. In another embodiment, edaravone is administered intravenously in the manner described at medlineplus.gov/druginfo/meds/a617027.html which is incorporated herein by reference in its entirety. In another embodiment, an oral dose of edaravone can be administered as described in U.S. Pat. No. 10,987,341 which is incorporated herein by reference in its entirety. In still another embodiment, edaravone can be formulated into a lipid based nanosystem as described by Parikh, et al., Drug Del., 24(1):962-978 (2017).

Combinations

The methods of this invention employ a synergistic combination of edaravone with a deuterated arachidonic acid or ester thereof or a prodrug thereof to significantly reduce the rate of decline in a patient suffering from ALS as compared to the use of each drug alone.

Edaravone may be administered concurrently with the deuterated arachidonic acid or prodrug or ester thereof, prior to deuterated arachidonic acid or prodrug or ester thereof, or after deuterated arachidonic acid or prodrug or ester thereof. The deuterated arachidonic acid or prodrug or ester thereof may be administered in the same formulation as edaravone, or the drugs may be administered in different formulations.

For example, deuterated arachidonic acid or prodrug or ester thereof may be administered periodically, e.g. daily, every other day, etc. The current recommended dosage of edaravone is 60 mg administered as an intravenous infusion (30 mg/100 mL) over 60 minutes. Edaravone may also be administered orally, for example between 50 mg/day and 150 mg/day, e.g. 60 mg/day or 105 mg/day. In some embodiments, edaravone is administered in an initial treatment cycle of daily dosing for 14 days followed by a 14-day drug-free period. In some embodiments, edaravone is administered in subsequent treatment cycles: daily dosing for 10 days out of 14-day periods, followed by 14-day drug-free periods.

In one embodiment, there is provided a method for reducing the rate of loss of functionality in a patient afflicted with ALS and undergoing treatment with edaravone which method comprises further treating said patient with an effective amount of a deuterated arachidonic acid or a prodrug thereof. When so administered, this combination reduces the rate of loss of functionality by more than the additive amount achieved by either drug alone.

In one embodiment, the form of administration of edaravone is not critical and any form that provides the desired therapy can be used. Such includes infusion administration, intravenous administration, oral delivery, transdermal delivery, intrapulmonary delivery, and the like.

In one embodiment, the deuterated arachidonic acid or ester thereof or a prodrug thereof having deuteration at the 13-position is administered as a D2-LA or an ester thereof. In vivo, a portion of D2-LA is bioconverted to D2-AA thereby providing the active deuterated D2-AA to the patient.

In one embodiment, D2-LA ethyl ester is administered in a tiered dosing schedule comprising a loading dose followed by a maintenance dose. The loading dose comprises from about 7 to about 12 grams per day of D2-LA which is orally delivered. The maintenance dose is less than the loading dose and is also orally delivered. Typically, the maintenance dose is no more than about 65% of the loading dose and preferably from about 30% to about 65% of the loading dose. The loading dose is continued for a period of time sufficient to achieve a steady state concentration of D2-AA in vivo which is typically at least about 30 day, or 45 days, or about 60 days from the start of therapy based on the attending clinician's evaluation. The specific timing for transitioning from the loading dose to the maintenance dose is at the discretion of the attending clinician. See, for example, allowed U.S. patent application Ser. No. 17/169,271, supra. Periodic analysis of the concentration of D2-AA in the red blood cells provides a basis for assessing whether the absorption of D2-LA followed by in vivo conversion of D2-LA to D2-AA is progressing appropriately can be done. See, for example, U.S. Provisional Patent Application Ser. No. 63/177,794 and PCT App. Nos. PCT/US22/15368 and PCT/US22/15366, each of which is incorporated herein by reference in its entirety.

In one embodiment, the amount of D2-LA or an ester thereof that is administered to the patient can be reduced to reflect the synergy achieved with the combination described herein. Although not preferred, dosing at levels of about 3 grams per day or 5 grams per day nevertheless evidence synergy when combined with edaravone.

As to D6-AA, such can be administered an ester prodrug or as D6-arachidonic acid or a pharmaceutically acceptable salt thereof. The drug is administered orally as described above. Again, periodic blood tests can be done to assess proper absorption of the drug. As above, a tiered dosing regimen is preferred. However, while not preferred, dosing at consistent amounts of the drug or prodrug can be used such as 0.6 grams per day.

In one embodiment, there is provided a method for reducing the rate of loss of functionality in a patient afflicted with ALS and undergoing treatment with an effective amount of a deuterated arachidonic acid or a prodrug thereof wherein said method comprises administering to said patient an effective amount of edaravone. When so administered, this combination reduces the rate of loss of functionality by more than the additive amount achieved by either drug alone. The methods for administration described above can be used.

In one embodiment, the edaravone and the deuterated arachidonic acid or a prodrug thereof can be combined into a formulation for administration to the patient for uptake of the drugs systemically. For example, D2-LA ethyl ester and D6-AA ethyl ester are both oils which can be used as a carrier for edaravone. For example, edaravone can be added to either of such oils and then the combination can be encapsulated into capsules or administered as an oil. In the latter case, the combination can further comprise a sweetener, a stabilizer, a colorant, and the like. For example, edaravone (as a free base) is added to D2-LA or D2-AA in an effective amount. The combination is agitated as necessary to provide for a homogenous oil solution. If necessary, especially for D2-AA, a small amount of a co-solvent such as AA can be intermixed to ensure homogenous solution.

Accordingly, in one embodiment, there is provided a composition suitable for administration to a patient which composition comprises D2-LA ester or D6-AA ester wherein the composition further comprises an effective amount of edaravone. Such a composition obviates the need to provide two separate drugs administered sequentially.

Disease Progression

In ALS, the reduction in the progression of this disease can be readily calculated by using the known and established rate functional decline measured by the R-ALS Functional Rating Scale-revised after commencement of drug therapy as compared to the rate of decline prior to drug therapy (natural history of decline). As the rate of decline is not perceptible on a day-to-day basis, the functional decline is typically measured monthly and is evaluated over a period of time such as every 1 to 24 months, such as every 3 months, every 6 months, or annually.

As set forth in the examples below, the rate of functional decline is predicated on measuring an individual's, or a cohort's, average for the natural history of disease progression. Next, the individual or cohort average for the functional decline is determined at a period of time such as at 3, 6 or 12 months after initiation of therapy. The rate of decline based on the average of the natural history of the cohort is set as the denominator. The numerator is set as the delta between the rate of the natural history of disease progression and the rate of functional decline after a set period of treatment per this invention. The resulting fraction is the multiplied by 100 to give a percent change. The following exemplifies this analysis.

Cohort A has an average natural history rate of decline in functionality of 28 annualized for a one (1) year period. Six (6) months after initiation of treatment per this invention, Cohort A an annualized average rate of decline in functionality has dropped to 14. This provides a delta of 14 degrees. So, using 14 as the numerator and 28 as the denominator and then multiplying result by 100, one obtains a reduction in the annualized rate of decline of 50 percent.

In general, the methods of this invention provide for an average percent change in reduction in functionality for a cohort of at least 30% and, more preferably, at least about 35%, or at least about 40%, or at least about 45%, or at least about 50%, or at least about 55%, or at least about 60%. In embodiments, the change in reduction of functionality is measured over a time period, for example, 3 months to 24 months, e.g., at 3 months, at 6 months, or annually. The rate of decline can be measured over any time period intermediate between 3 months and 1 year.

Kit of Parts

The methods described herein can be practiced using a kit of parts. For example, edaravone either as an injectable or as an infusion is designed to be administered one a day for 10 days followed by 18 days without administration. When edaravone is used for oral delivery in a capsule, e.g., gel capsule, then the kit of parts comprise a first set of edaravone capsules and a second set of capsules for the deuterated arachidonic acid or a prodrug thereof. In the case of D2-LA esters, the second set will contain a plurality of capsules for administration each day.

In one embodiment, the kit of parts can contain a first row containing 60 mg dose of edaravone in one capsule or two capsules containing 30 mg each. A second row could contain 9 capsules of D2-LA ester each containing 1/9 the daily dose. These capsules could be split into 3 groups of three capsules where each group is separated from the next group so as to define three separate dosings—morning, noon and evening. In one embodiment, the edaravone capsule is colored to differentiate from the D2-LA ester capsules. For example, the edaravone capsule can be colored red and the D2-LA ester capsules colored green. The kit of parts may contain only a single day of dosing or multiple days of dosing per container or multiple days of dosing per container. Each of these containers could be labeled to indicate that the dosing contained therein is to be taken prior to any dosing of the D2-LA ester alone ("First Container(s)"). Preferably, the maximum number of doses for the combination in a single container is no more than 10 days for any given 28-day dosing period. This will prevent continued dosing of edaravone past the 10-day dosing period. It is understood that when the maintenance dose of D2-LA ester is used, the number of capsules required for administration could be reduced or not. In the case where the number of capsules is not reduced, then either the capsule size can be reduced, or a pharmaceutically acceptable excipient can be added to the capsules.

The kit of parts could contain a further container or additional containers ("Second Container(s)") each of which contains a single day dosing amount of the D2-LA ester or multiple days of dosing. The Second Container(s) would include the remaining doses for the rest of the 28-day dosing period. Preferably, the Second Containers are labeled to indicate that these containers are not to be used until after the doses in the First Container(s) have been taken. The dosing of D2-LA ester in the Second Container can be arranged as in the First Container and colored the same.

In the case of D6-AA ester, the amount of drug required for therapy is contemplated to be less than that of D2-LA ester as described above. Accordingly, in this embodiment, the kit of parts will be substantially similarly to that described above but for the fact that there will be fewer capsules for the D6-AA ester than for the D2-LA ester.

In one embodiment, capsules could contain a combination of edaravone either mixed or solubilized into the deuterated arachidonic acid or a prodrug thereof. In such a case, the kit of parts would comprise a container a first set of capsules wherein the daily dose of edaravone is included in the capsules containing D2-LA ester ("First Set of Capsules"). In one embodiment, this First Set of Capsules would have the dosing of edaravone in a single capsule or partitioned into the number of capsules required for D2-LA ester. For example, if the dose of D2-LA requires 9 separate capsules, then the entire dose of edaravone could be partitioned into 1 capsule, 3 capsules, 6 capsules, or 9 capsules. Any subset of capsules containing edaravone would need to be appropriately colored to distinguish from those capsules that do not. As above, the maximum number of doses in such a container would be ten in order to meet the dosing requirements now in place for edaravone. Alternative, the First Set of Capsules for each day during the 10-day period could be provided in a single daily container, a multiple day container (e.g., 5 days) or a single container for all 10 days. It is understood that when the maintenance dose of D2-LA ester is employed, the number of capsules The kit of parts could contain a further container or additional containers for the capsules to be used from day 11 to day 28 of the treatment plan ("Second Set of Capsules"). In one embodiment, the daily dose of the Second Set of Capsules could be included in a single day container or a multiple day container. Preferably, the container(s) for the Second Set of Capsules is labeled to indicate that this container or containers is/are not to be used until after doses provided by the First Set of Capsules have been taken. The dosing of D2-LA ester in these containers can be arranged in the same format as described above (3×3). As above, when the maintenance dose is to be used, the number of capsules can be reduced or retained the same using less active per capsule.

In the case of D6-AA ester, the amount of drug required for therapy is contemplated to be less than that of D2-LA ester as described above. Accordingly, in this embodiment, the kit of parts will be substantially similarly to that described above but for the fact that there will be fewer capsules for the D6-AA ester than for the D2-LA ester.

When edaravone is administered as an injectable composition, the kit of parts can contain both a single day dose of the D2-LA ester or the D6-AA ester as described above as well as a syringe containing the injectable edaravone composition or multiple daily doses. In one embodiment, the kit of parts can contain a primary container or containers that hold multiple syringes up to a maximum of 10 and a corresponding number of daily doses of the D2-LA ester or the D6-AA ester. As above, the primary container or containers limit the number of syringes to 10 and the capsules containing either ester can be arranged as previously described. A secondary container or containers can contain the remaining 18 days of capsules containing either ester to ensure a full 28-day pharmaceutical dosing regimen.

As is apparent, the specifics for containers in each kit of parts embodiments can be varied provided that there is provided a specific dose of edaravone sufficient to meet the stated dosing regimen of 60 mg per day for 10 days and either a loading dose or a maintenance dose of the D2-LA ester or the D6-AA ester for all 28 days of the dosing regimen. It is contemplated that sufficient containers can be provided such that multiple 28 days of the dosing regimen can be shipped to a hospital, pharmacy, the attending clinician, the patient's care giver or the patient.

The container used is not critical and can include blister packs for capsules, closed boxes comprising paper, plastic, or metal, one or more bottles, and the like. The container should be appropriately labeled and/or contain such a label to ensure that the care giver or patient is instructed to the proper administration of both drugs.

EXAMPLES

The methods and compositions described herein are further understood by reference to the following examples, which are intended to be purely exemplary of this invention. These methods and compositions are not limited in scope by the exemplified embodiments, which are intended as illustrations of single aspects of this invention only. Any methods and compositions that are functionally equivalent are deemed to be equivalents. Various modifications of this invention in addition to those described herein will become apparent to those skilled in the art from the foregoing description and accompanying figures. Such modifications fall within the scope of the appended claims. In these examples, the following terms are used herein and have the following meanings. If not defined, the abbreviation has its conventional medical meaning.

| | |
|---|---|
| D2-AA = | 13,13-D2-Arachidonic Acid |
| D6-AA = | As defined herein |
| AA = | Arachidonic Acid |
| ALS = | Amyotrophic lateral sclerosis |
| ALSFRS-R = | Revised ALS Functional Rating Scale |
| D2-LA = | 11,11-D2-Linoleic Acid |
| LA = | Linoleic Acid |
| LPO = | Lipid Peroxidation |
| Radicava ® = | an edaravone infusion formulation sold by Mitsubishi Tanabe, Inc., Osaka, Japan |
| RBCs = | Red Blood Cells |

Example 1—Evidence of Synergy Using a Combination of Therapy of D2-AA and Edaravone This example reports the results of an expanded access program treating 13 patients with ALS with D2-LA. Of these 13 patients, 5 patients were also treated both before and during therapy with D2-LA with edaravone and 8 patients were treated only with D2-LA during the treatment protocol. While the current dosing regimen employs a loading dose of about 8.64 grams/day of D2-LA for about 1 month followed by a maintenance dose of about 4.80 grams/day or about 5.76 gram/day of D2-LA during the maintenance phase, the patients in this study were all treated with a daily dose of 2.88 gram/day LA for two weeks to assure drug tolerability followed by a dose of 5.76 grams/day of D2-LA for the remainder of the study.

Before initiation of therapy, the functionality of each patient was evaluated using the ALSFRS-R scoring system and the initial scores recorded. After at least 6 months from the start of therapy, the functionality for each patient was reevaluated again using the ALSFRS-R scoring system.

The patients were broken down into two groups as follows:
1. Those on edaravone both before and during therapy with D2-LA;
2. Those not on edaravone either before or during therapy with D2-LA.

The ALSFRS-R scores between just before start of therapy were then compared between the two groups based on the scores obtained after 6 months of therapy. Table 1 below provides the average results in the ALSFRS-R scores after 6 months of treatment for patients treated with D2-AA alone (8 patients) as well as for patient treated with D2-AA plus edaravone (5 patients).

TABLE 1

| Patients treated | Delta between Average Score at Start of Therapy Compared to 6 months after Start of Therapy |
|---|---|
| Treatment with only D2-LA (no edaravone) | −7.0 |
| Treatment with D2-AA + edaravone | −2.0 |

To evaluate the benefit associated with edaravone pre-treatment in the second group of patients, reference is made to FIG. 1 which provides data from the manufacturer of edaravone (Mitsubishi Tanabe). That data states that over a 6-month period, edaravone provides a 2.49 score benefit over control. As these patients were pre-treated with edaravone before the start of therapy with D2-LA, the minimum synergistic results would be those that assume that pre-treatment did not reach 6 months before the start of D2-LA administration. When so assumed, a portion of the benefit of edaravone treatment would need to be accounted for in the reported numbers for the natural history. Nevertheless, even attributing the entire 2.49 score units benefit provided by edaravone in the above treatment of D2-LA, there exists a benefit achieved with the combination of these two drugs that is still more than 2.5 score units better than the additive effect. This difference is attributed to synergy. Assuming that such pre-treatment with edaravone for these patients was more than 6 months prior to treatment with D2-LA, then the entire benefit achieved by edaravone would have been fully accounted for in the patient's natural history score. As such, the synergy achieved by these to drugs in combination provided for a 5 point benefit over the additive benefit of each drug alone.

Still further, recognizing that the dosing of D2-LA in this study did not utilize the current dosing regimen, further improvements evidencing contemplated additional synergy may be obtained.

Alternatively, the synergy evidenced above can allow for dose sparing of D2-LA from 8.64 grams per day to say about 5.76 grams per day or less and still see a significant synergistic benefit.

Example 2

This example assesses the relative reduction in LPO in an inflammation model to provide for an assessment of the relative activity of D2-AA (obtained by bioconversion of D2-LA) as compared to D6-AA.

Specifically, it is well understood that inflammation plays a significant role in many neurodegenerative diseases. In this example, LPS administration is known to promote inflammation through various mechanisms including secretion of pro-inflammatory cytokines, eicosanoids and induction of ROS. This example employed LPS to ascertain the extent of inflammation arising from ROS induced oxidation of H-AA versus D2-AA (achieved by administration of D2-LA) versus D6-AA in the lungs of mice. Specifically, four groups of mice were used. The first group was control mice treated with H-LA control mice. The second group of mice received a 6-week course of D2-LA. It is understood that in vivo conversion of a portion of both H-LA and D2-LA occurs to provide for AA and 13,13-D2-AA respectively. The third group of mice received a 6-week course of H-AA. The fourth group of mice received a 6-week course of D6-AA.

All groups then received a single intranasal administration of LPS to induce acute lung inflammation. The degree of the inflammatory response was based on the interalveolar septa distance where the larger the distance of the septa, the greater the degree of inflammation. The animals were sacrificed and the interalveolar septa distance was measured. Table 2 provides an average degree of spatial distance for the interalveolar septa for the results of all groups.

TABLE 2

|  | H-LA | D-LA | H-AA | D-AA |
|---|---|---|---|---|
| Interalveolar space | 14.2 µm | 10.7 µm | 9.1 µm | 4.1 µm |

The above results evidence about a 25% reduction in the spatial distance for the interalveolar septa for the mice treated with D2-AA (by administration of the D2-LA prodrug) relative to those treated with H-LA. However, the mice treated D6-AA had almost a 60% reduction in the same spatial distance evidencing the benefits of D6-AA in treating inflammation.

The above data infers that D6-AA provides at least 2× the benefit than that of D2-AA in this inflammation model. Such data is used as a basis to estimate the protection against LPO accorded by D6-AA as compared to D2-AA.

Using this data, the amount of D6-AA required to achieve a similar result to D2-LA can be projected to be one-tenth of 8.64 grams/day (due to obviating the need for bioconversion)×0.5 (accounting for about twice the activity of D6-AA versus D2-AA) or 0.43 grams per day. Still further, given that 5.76 grams of D2-LA biogenerated sufficient D2-AA to provide for synergy with edaravone, one can take (5.76 grams per day for synergy/8.64 grams per day for the loading dose and assess that with D6-AA requires only 0.43 g per day×(5.76/8.64)=0.29 grams per day or, alternatively, 0.05 grams per day, will provide for synergistic results.

What is claimed is:

1. A method for reducing the rate of disease progression of ALS in a patient the method comprising administering to the patient a therapeutically effective amount of 3-methyl-1-phenyl-2-pyrazoline-5-one or a pharmaceutically acceptable salt thereof in combination with a therapeutically effective amount of a deuterated arachidonic acid or a prodrug thereof; wherein the rate of disease progression in the patient is less than the aggregate achieved by either drug; and wherein the deuterated arachidonic acid or a prodrug thereof is administered using a dosing regimen that includes a loading dose and a maintenance dose.

2. A method for reducing the rate of loss of functionality in an ALS patient being treated with a therapeutically effective amount of a deuterated arachidonic acid or a prodrug thereof the method comprising further administering a therapeutically effective amount of 3-methyl-1-phenyl-2-pyrazoline-5-one or a pharmaceutically acceptable salt thereof; wherein the rate of loss of functionality in the patient is less than the aggregate achieved by either drug; and wherein the deuterated arachidonic acid or a prodrug thereof is administered using a dosing regimen that includes a loading dose and a maintenance dose.

3. A method for reducing the rate of loss of functionality in an ALS patient being treated with a therapeutically effective amount of 3-methyl-1-phenyl-2-pyrazoline-5-one or a pharmaceutically acceptable salt thereof the method comprising further administering a therapeutically effective amount of a deuterated arachidonic acid or a prodrug thereof; wherein the rate of loss of functionality in the patient is less than the aggregate achieved by either drug; and wherein the deuterated arachidonic acid or a prodrug thereof is administered using a dosing regimen that includes a loading dose and a maintenance dose.

4. The method of claim 1, wherein said deuterated arachidonic acid prodrug is 11,11-D2-linoleic acid or an ester thereof.

5. The method of claim 4, wherein said ester is a C1-C6 alkyl ester.

6. The method of claim 1, wherein said deuterated arachidonic acid or a prodrug thereof is an ester of 7,7,10,10,13,13-D6-arachidonic acid.

7. The method of claim 6, wherein said ester is a C1-C6 alkyl ester.

8. The method of claim 1, wherein said deuterated arachidonic acid is 7,7,10,10,13,13-D6-arachidonic acid or a pharmaceutically acceptable salt thereof.

9. The method of claim 4, wherein 11,11-D2-linoleic acid ethyl ester is administered daily at a dose of about 5.5 to about 12 grams/day during the loading phase and then at a dose that is from about 30% to about 65% of the loading dose during the maintenance phase of the dosing regimen.

10. The method of claim 9, wherein 3-methyl-1-phenyl-2-pyrazoline-5-one or a pharmaceutically acceptable salt thereof is administered as an infusion, an injectable composition, an oral composition or in combination with said deuterated arachidonic acid or a prodrug thereof.

11. The method of claim 1, wherein said deuterated arachidonic acid or a prodrug thereof is 7,7,10,10,13,13-D6-arachidonic acid, a pharmaceutically acceptable salt thereof or an ester thereof.

12. The method of claim 11, wherein said deuterated arachidonic acid prodrug is 7,7,10,10,13,13-D6-arachidonic acid ethyl ester.

13. The method of claim 1, wherein 7,7,10,10,13,13-D6-arachidonic acid or ester thereof is administered daily at a dose of about 0.05 to about 5 grams/day during the loading phase and then at a dose that is from about 30% to about 70% of the loading dose during the maintenance phase of the dosing regimen.

14. The method of claim 13, wherein 7,7,10,10,13,13-D6-arachidonic acid or ester thereof is administered daily at a dose of about 0.5 to about 5 grams/day during the loading phase.

15. The method of claim 13, wherein 3-methyl-1-phenyl-2-pyrazoline-5-one or a pharmaceutically acceptable salt thereof is administered as an infusion, an injectable composition, an oral composition.

16. The method of claim 1, wherein 3-methyl-1-phenyl-2-pyrazoline-5-one or a pharmaceutically acceptable salt thereof is administered as an injectable composition or an oral composition.

17. The method of claim 1, wherein 3-methyl-1-phenyl-2-pyrazoline-5-one or a pharmaceutically acceptable salt thereof is administered as an oral composition in combination with deuterated arachidonic acid or a prodrug thereof.

18. The method of any one of claims 1, 2 or 3, wherein the method further comprises restricting the patient's consumption of excessive dietary polyunsaturated fatty acids during administration of said deuterated arachidonic acid.

* * * * *